United States Patent [19]
Gozani

[11] Patent Number: 5,752,512
[45] Date of Patent: May 19, 1998

[54] APPARATUS AND METHOD FOR NON-INVASIVE BLOOD ANALYTE MEASUREMENT

[75] Inventor: Shai N. Gozani, Brookline, Mass.

[73] Assignee: Massachusetts Institute of Technology, Cambridge, Mass.

[21] Appl. No.: 435,403

[22] Filed: May 10, 1995

[51] Int. Cl.[6] .................................................. A61B 05/00
[52] U.S. Cl. ........................ 128/635; 128/630; 128/741
[58] Field of Search ................................. 128/641, 635, 128/630, 632, 741

[56] References Cited

U.S. PATENT DOCUMENTS

| | | | |
|---|---|---|---|
| 4,317,817 | 3/1982 | Blohm et al. | 424/226 |
| 4,392,933 | 7/1983 | Nakamura et al. | 204/403 |
| 4,431,004 | 2/1984 | Bessman et al. | 128/635 |
| 4,436,094 | 3/1984 | Cerami | 128/635 |
| 4,882,492 | 11/1989 | Schlager | 250/346 |
| 5,050,612 | 9/1991 | Matsumura | 128/670 |
| 5,131,401 | 7/1992 | Westenskow et al. | 128/741 |
| 5,139,023 | 8/1992 | Stanley et al. | 128/637 |
| 5,267,152 | 11/1993 | Yang et al. | 364/413.09 |
| 5,322,063 | 6/1994 | Allen et al. | 128/635 |
| 5,360,004 | 11/1994 | Purdy et al. | 128/633 |
| 5,368,028 | 11/1994 | Palti | 128/635 |
| 5,379,764 | 1/1995 | Barnes et al. | 128/633 |

FOREIGN PATENT DOCUMENTS

| | | |
|---|---|---|
| 0 025 222 A2 | 3/1981 | European Pat. Off. . |
| 0 282 234 A1 | 9/1988 | European Pat. Off. . |
| 0 436 121 A1 | 7/1991 | European Pat. Off. . |
| WP 91/16001 | 10/1991 | WIPO . |
| WO 92/03974 | 3/1992 | WIPO . |

OTHER PUBLICATIONS

Roy Testerman, "Method of Measuring Blood Glucose Level by Sensing Evoked Action Potentials in Peripheral Nerve," *Research Disclosure*, 227:92, Article No. 22728 (Mar. 1983).

International Search Report, PCT/US96/04840 dated Aug. 21, 1996.

Williams & Wilkin, "*Muscles Alive; Their Functions Revealed by Electromyography*", John V. Basmajian, M.D., fifth edition, 1985, pp. v, 19–65.

Institute of Physiology, University of Munich, "*Glucose availability and sensitivity to anoxia of isolated rat peroneal nerve*", M. Strupp et al., 1991, pp. E389–E394.

Journal of Physiology, "Changes in Excitability and Accommodation of Human Motor Axons Following Brief Periods of Ischaemia", H. Bostock et al., 1991, pp. 513–535.

*Acta Physiol Scand*, "Mechanism of anoxic conduction block in mammalian nerve", P. Lindström and T. Brismar, 1991, pp. 429–433.

*Acta physiol scand*, "Decremental Conduction in Normal Nerves Subjected to Ischemia?", V.K. Nielsen, T. Kardel, 1974, pp. 249–262.

*J. Neurol Neurosurg Psychiat*, "refractory and supernormal periods of the human median nerve", R.W. Gilliatt R.G. Willison, 1963, pp. 136–147.

University of Florida, "*Effect of Oxygen lack on the Single Isolated Mammalian (Rat) Nerve Fiber*", J. Maruhashi, E.B. Wright, 1996, pp. 434–452.

*J. Neurol Neurosurg Psychiat*, "The effect of ischaemia on the excitability of human sensory nerve", K.N. Seneviratne, O.A. Peiris, 1968, pp. 338–347.

(List continued on next page.)

*Primary Examiner*—Robert L. Nasser
*Attorney, Agent, or Firm*—Testa, Hurwitz & Thibeault, LLP

[57] ABSTRACT

A non-invasive blood analyte concentration monitor. The monitor includes a stimulator applying a stimulus to an endogenous tissue responsive to the stimulus and a detector for detecting a response of an endogenous tissue to the stimulus. Also provided is a correlator which correlates the detected response of the endogenous tissue to an analyte concentration. In one embodiment, the monitored blood analyte is glucose.

18 Claims, 11 Drawing Sheets

OTHER PUBLICATIONS

*Journal of Neurochemistry*, "Substrate Changes in Peripheral Nerve During Ischaemia and Wallerian Degeneration", M. Stewart, J. Passonneau and O. Lowry, vol. 12, 1965, pp. 719–727.

"Clinical Electromyography: Nerve Conduction Studies", S.J. Oh, MD., Second Edition, 1993, pp. 1–2 and 26–59.

*Clinical Chemistry*, "Noninvasive Glucose Monitoring in Diabetic Patients: A Preliminary Evaluation", M.R. Robinson, et al. vol. 38, No. 9, 1992, pp. 1618–1622.

*Electroencephalography and clinical Neurophysiology*, "Threshold tracking provides a rapid indication of ischaemic resistance in motor axons of diabetic subjects", P. Weigl, et al., 1989, pp. 369–371.

Diabetes, "In Vitro Studies of the Substrates for Energy Production and the Effects of Insulin on Glucose Utilization in the Neural Components of Peripheral Nerve ", D. Green, A. Winegrad, vol. 28, 1979, pp. 878–887.

*Journal of the Neurological Sciences*, "Studies of resistance to ischemic nerve conduction failure in normal and diabetic rats", G. Parry, H. Kohzu, 1989, pp. 61–67.

*Journal of the Neurological Sciences*, "The Susceptibility of rat diabetic nerve to ischemia: increased or decreased?" H. Nukada, 1993, pp. 162–168.

*Clinical Chemistry*, "An Overview of Minimally Invasive Technologies", B. Ginsberg, vol. 38, No. 9, 1992, pp. 1596–1600.

*Annals of Internal Medicine*, "Nerve Conduction Abnormalities in Untreated Maturity–Onset Diabetes: Relation to Levels of Fasting Plasma Glucose and Glycosylated Hemoglobin", R. Graf, et al., 1979, pp. 298–303.

*Acta Neurol Scand*, "Peripheral nerve function during hyperglycemic clamping in healthy subjects", S.H. Sindrup, et al., 1988, pp. 141–145.

*Journal of Neurology*, Neurosurgery, and Psychiatry, "Effect of ischaemia on peripheral nerve function in patients with chronic renal failure undergoing dialysis treatment", P. Gastaigne et al., 1972, pp. 631–637.

*J. Physiol*, "Effects of Changes of Blood Pressure, Respiratory Acidosis and Hypoxia on Blood Flow in the Sciatic Nerve of a Rat", P.A. Low et al., 1984, pp. 513–524.

*Journal of Physiology*, "The Effects of Hyperglycemic hypoxia on rectification in rat dorsal root axons", P. Grafe et al., 1994, pp. 297–307.

*Journal of Neurology, Neurosurgery, and Psychiatry*, "The relationship between peripheral nerve resistance to ischaemia and diabetic control", D.E. Price et al., 1987, pp. 1671–1673.

*Neurology*, "Ischemia and sensory nerve conduction in diabetes mellitus", S.H. Horowitz, M.D. et al., 1979, pp. 695–704.

*Diabetologia 4*, "Variations in Motor Conduction Velocity Produced by Acute Changes of the Metabolic State in Diabetic Patients", G. Gregersen, 1968, pp. 273–277.

*American Physiological Society*, "Ischemic conduction failure and energy metabolism in experimental diabetic neuropathy", P.A. Low et al., 1985, pp. E457–E462.

*American Neurological Association*, "Differences in Sensitivity to Hyperglycemic Hypoxia of Isolated Rat Sensory and Motor Nerve Fibers", U. Schneider et al., 1992, pp. 605–610.

*Diabetes Care*, "Glycemic Control and Diabetic Complications", S. Strowig, RN, MSN et al., vol. 15, No. 9, 1992, pp. 1126–1140.

*Arch Neurol*, "The Use of Sensory Action Potentials in the Diagnosis of Peripheral Nerve Disease", J. Shefner MD, et al., vol. 47, 1990, pp. 341–348.

*Journal of Neurochemistry*, "Rabbit Sciatic Nerve Fascicle and 'Endoneurial'Preparations for In Vitro Studies of Peripheral Nerve Glucose Metabolism", D. Greene et al., 1979, pp. 1007–1018.

*J. Neurol. Neurosurg Psychiat*, "Vibratory perception during ischaemia in uraemic patients and in subjects with mild carbo–hydrate intolerance", N.J. Chistensen et al., 1969, pp. 519–524.

*Journal of Neurochemistry*, "Physiological and Biochemical Changes in Frog Sciatic Nerve During Anoxia and Recovery", Y. Okada et al., vol. 18, 1971, pp. 2335–2353.

*The Journal of Hand Surgery*, "New finger cuffs for use with digital tourniquets", J.A. McEwen, PhD. et al., 1988, pp. 888–892.

*The Journal of Hand Surgery*, "The digital tourniquet: How safe is it?", J.D. Lubahn, M.D. et al., 1985, pp. 664–669.

*Brain*, "Differences in behavior of sensory and motor axons following release of ischaemia", H. Bostock et al., 1994, pp. 225–234.

*Journal of Physiology*, "Hyperglycemic Hypoxia Alters After–Potential and Fast K+ Conductance of Rat Axons by Cytoplasmic Acidification", U. Schneider et al., 1992, 679–697.

*Journal of the Neurological Sciences*, "Is resistance to ischaemia of motor axons in diabetic subjects due to membrane depolarization?", M. Strupp et al., 1990, pp. 271–280.

*National Institutes of Health*, "Monitoring Blood Glucose with a Visual Stimulus", Abstract, one page.

*Diabetes Care*, "Implications of the DCCT, Looking beyond tight control", Richard R. Rubin, PhD. et al., vol. 17, No. 3, Mar. 1994, pp. 235–236.

*Kyoto World Congress Supplement*, "Noninvasive measurement of blood glucose concentrations by analyzing Fourier transform infra–red absorbance spectra through oral mucosa", K. Kajiwara et al., six pages, Jul. 1993.

*Journal of Prosthetic Dentistry*, "Surface electromyographic electrode pair with built–in buffer amplifiers", M. Fujisawa et al., vol. 63, No. 3, Mar. 1990, pp. 350–352.

Miles, *Glucometer Elite Diabetes Care System*, one page advertisement, 1994.

*Boehringer Mannheim Corporation*, Accu–Chek® blood glucose monitoring systems, two page advertisement, 1994.

*LifeScan Inc.*, One Touch® Basic Blood Glucose Monitoring System, one page advertisement, 1995.

*American Diabetes Association*, "Diabetes: 1993 Vital Statistics" and Direct and Indirect Costs of Diabetes in the United States in 1992, one page book advertisement.

*Medisense*, Companion™ 2, two page advertisement, not dated.

*IEEE Transactions on Biomedical Engineering*, "Clinical Application of an Active Electrode Using an Operational Amplifier", S. Nishimura et al., vol. 39, No. 10, 1992, pp. 1096–1099.

*Muscle & Nerve*, "Resistance to Ischemic Conduction Block of the Peripheral Nerve in Hyperglycemic Rats: An Electrophysiological Study", pp. 582–587.

*Brain Research*, "Contribution of Electrogenic Sodium–Potassium ATPase to Resting Membrane Potential of Cultured Rat Skeletal Myotubes", C. Brodie et al., 1985, pp. 28–35.

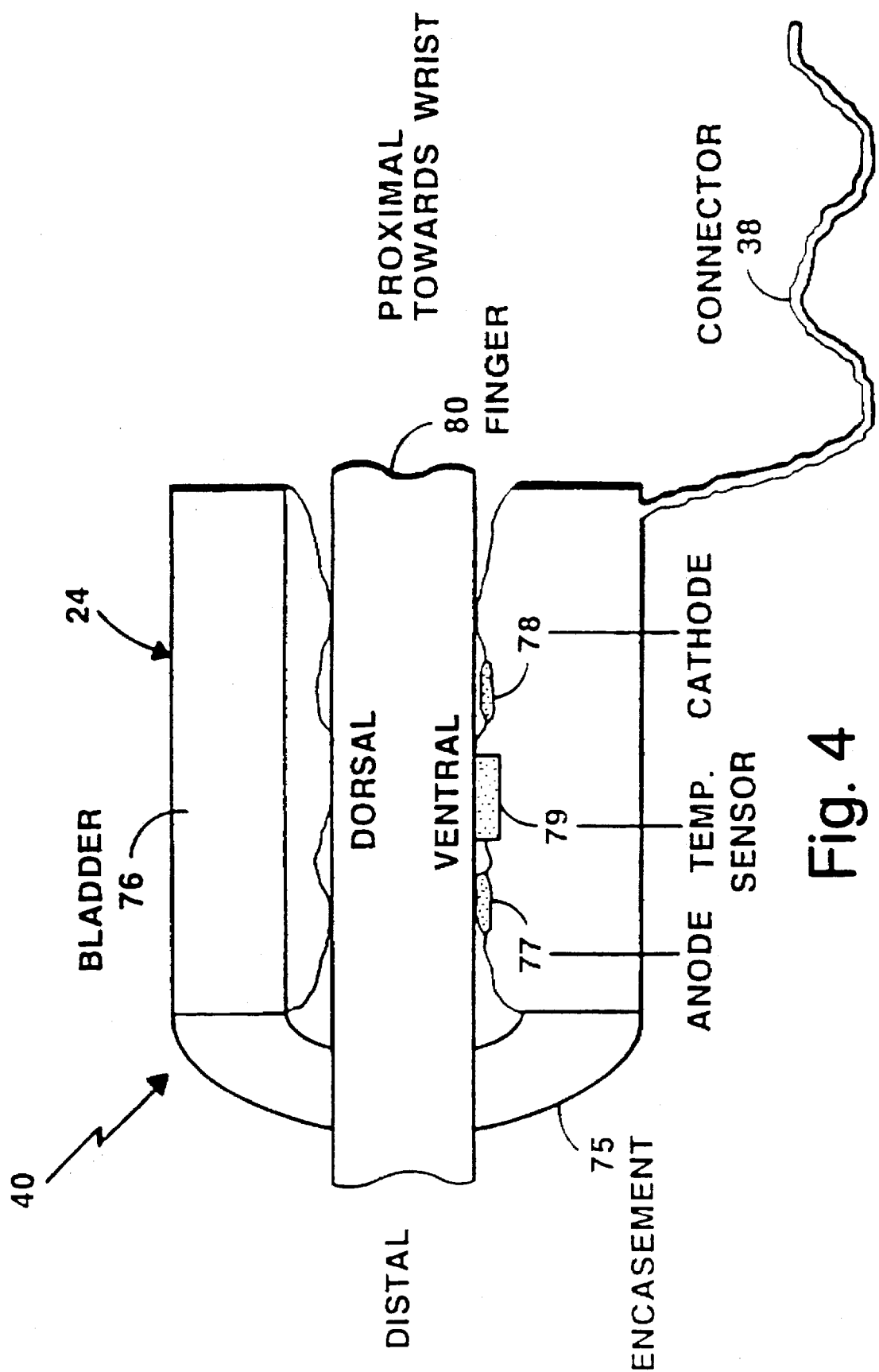

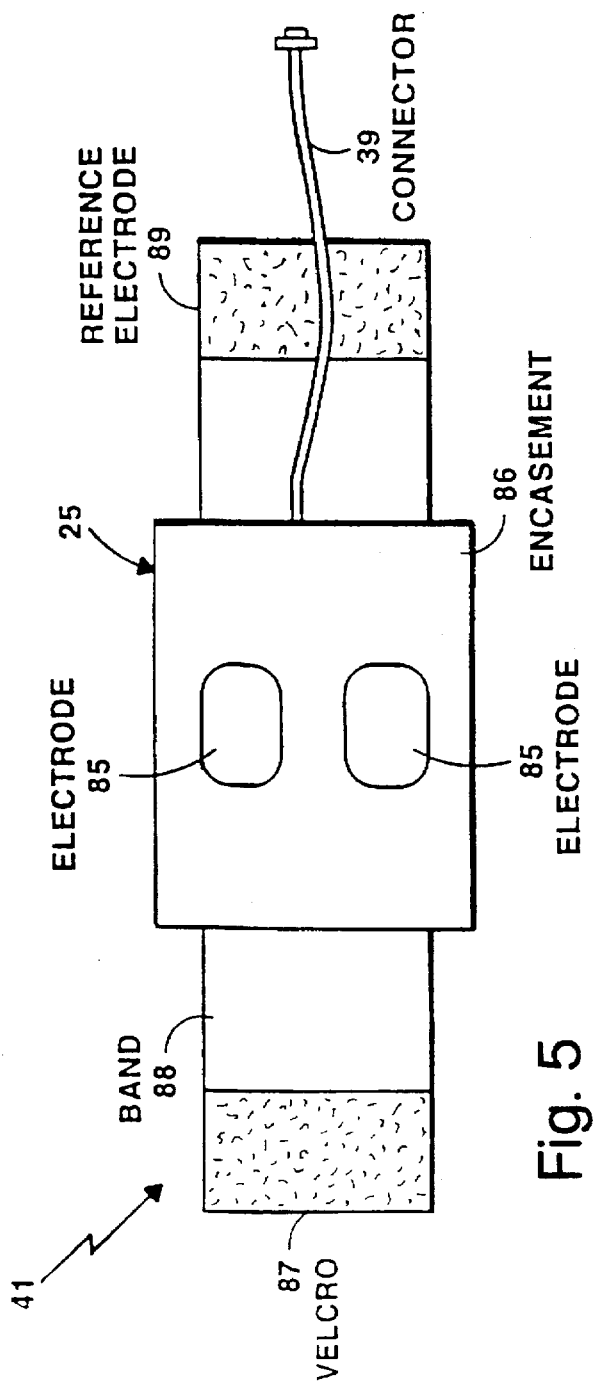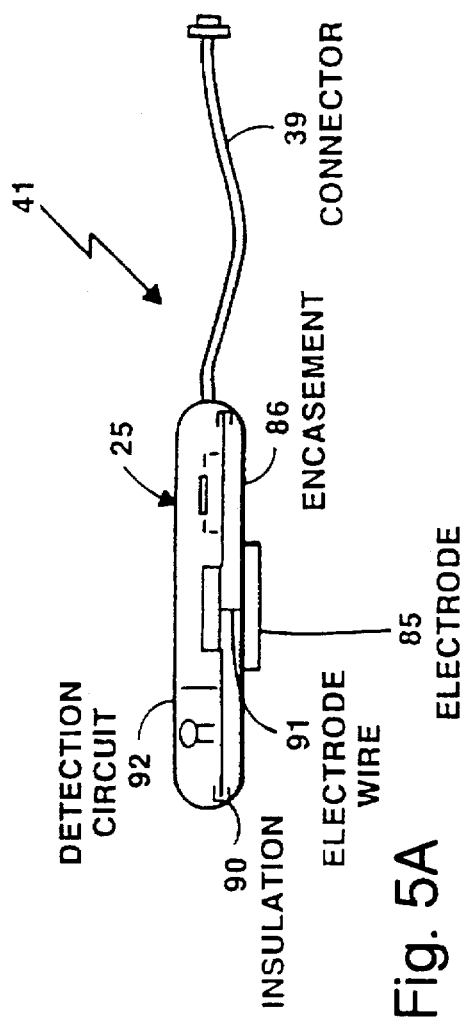

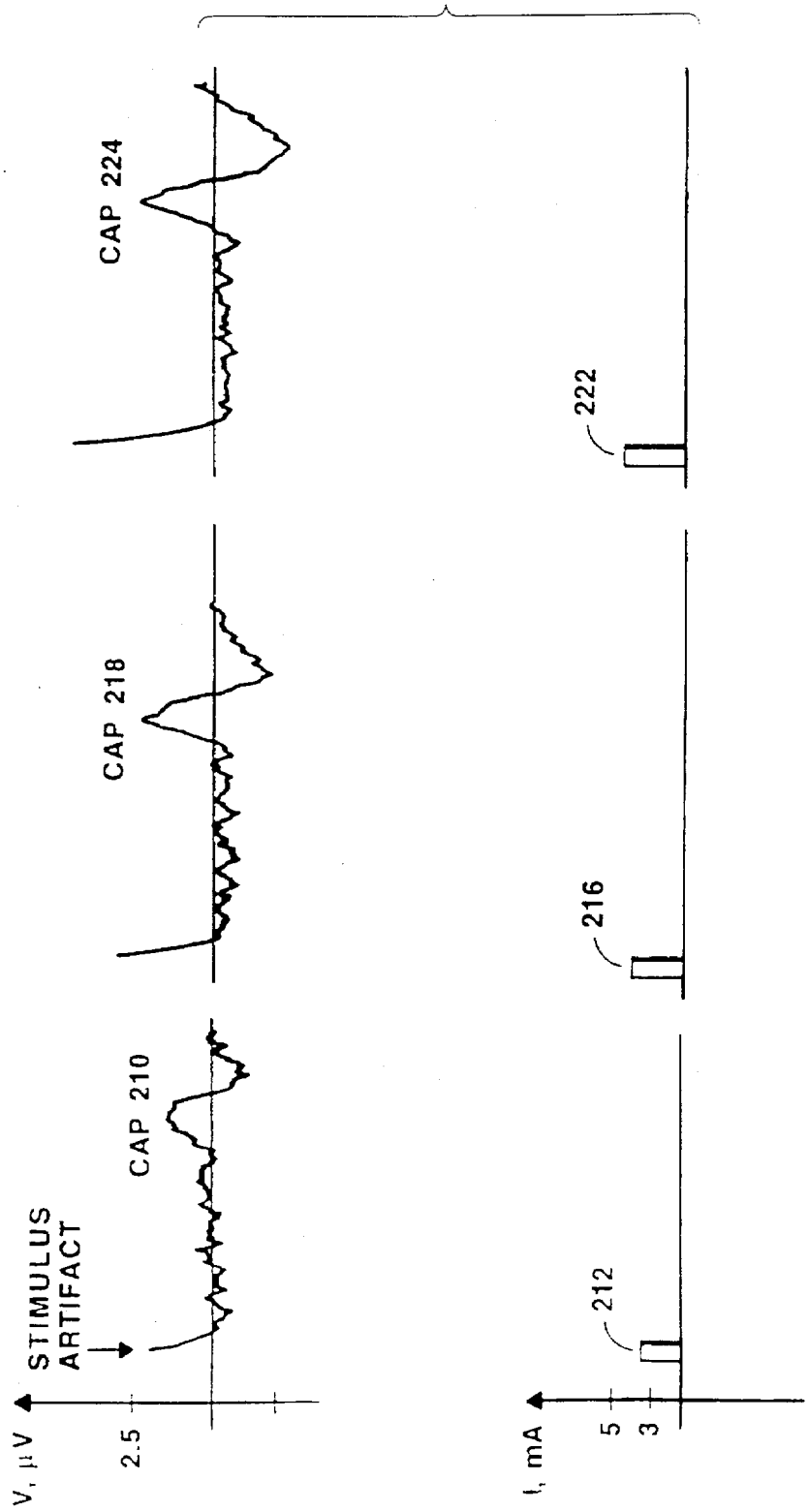

APPARATUS AND METHOD FOR NON-INVASIVE BLOOD ANALYTE MEASUREMENT

FIELD OF THE INVENTION

This invention relates generally to blood analyte monitoring in humans and, more specifically, to non-invasive apparatus and methods for monitoring a blood analyte, such as glucose in diabetic individuals.

BACKGROUND OF THE INVENTION

The use of real-time physiological data for evaluating options and making decisions about the treatment of a variety of medical conditions is appealing to both patients and health professionals. Technologies that obtain such data in non-invasive ways are particularly attractive because they minimize patient discomfort and nearly eliminate the possibility of infectious contamination. In those situations where frequent monitoring is required, such as Diabetes Mellitus, non-invasive technologies are particularly important.

Diabetes Mellitus is a common disease that afflicts 14 million people in the United States and several times that in the industrialized world. There are several different types of diabetes, however they all share a common metabolic dysfunction. Individuals with diabetes do not regulate the concentration of glucose within their blood in a normal physiological fashion. In particular, diabetics tend to have a high blood glucose concentration. This condition is called hyperglycemia and is caused by a lack of insulin, a reduced level of insulin or a resistance to the action of insulin. Diabetes Mellitus is associated with a high degree of morbidity including cardiac disease, renal disease, retinal disease and neurological disease. The cost of these complications to individuals and to society are severe.

There is no cure for Diabetes Mellitus. However, effective treatment modalities exist. A common goal of all treatment approaches is maintenance of blood glucose concentration within normal physiological limits. This is most often accomplished through a combined use of diet and therapeutic drugs such as insulin and/or oral hypoglycemics. The recently completed Diabetes Control and Complications Trial (DCCT) has conclusively demonstrated that any degree of normalization of blood glucose levels reduces long term diabetes associated morbidity. An essential element of such a normalization is frequent measurement of the blood glucose concentration. In intensive treatment programs, these blood glucose concentrations are used to acutely alter insulin doses. In less intensive programs, the measurements are recorded and provide very useful information that aids the physician in adjusting and fine tuning the individual diabetic's treatment plan.

Conventional self-monitoring of glucose by diabetic individuals can be divided into approaches that analyze fluids extracted from the body and those do not require bodily fluids. These approaches can be further subdivided into invasive and non-invasive techniques. Invasive techniques involve breaking the skin barrier and generally require that a sample of blood be obtained from the individual; whereas, non-invasive techniques do not require the skin barrier to be broken.

Systems for measuring glucose in bodily fluids are generally based on the oxidation of glucose by oxygen in the presence of glucose oxidase. The concentration of glucose is determined by correlation with the amount of particular byproducts of this reaction. The most common measurement is that of electrical energy produced by the oxidation reaction and measured by electrodes. Such approaches are the subject of U.S. Pat. Nos. 4,392,933 to Nakamura et al., 4,436,094 to Cerami and 4,431,004 to Bessman et al. The electrical energy can be measured by an electronic device and converted to a glucose concentration that is displayed.

Blood is the standard bodily fluid used for glucose oxidase based measurement of glucose concentration in diabetics. The disadvantage of this approach is that it is invasive because it requires a sample of the individual's blood. This sample is usually obtained from well vascularized tissue, such as a finger tip, with a small lancet. This process is quite painful and unacceptable to many diabetics. In addition to the physical discomfort, this procedure may result in scarring of the finger tips, is undesirable from an infectious disease perspective, is often embarrassing, and tends to be inconvenient.

Recently, techniques for obtaining bodily fluids non-invasively have been proposed. For example, U.S. Pat. No. 5,139,023 describes a system for measuring glucose in fluid obtained through the skin or a mucosal membrane. The major disadvantage of this and similar approaches is that the bodily fluid thus obtained may have a delayed and variable relation to the blood glucose concentration.

All approaches that measure glucose in a sample of bodily fluid have the additional disadvantage that each sample requires a separate disposable test-strip. This is necessary to minimize the possibility of transmitting infectious material. These disposable elements represent the major expense in current blood glucose monitoring technology. This expense may influence diabetics to minimize the frequency with which they monitor their blood glucose.

The aforementioned disadvantages of bodily fluid based measurement of glucose have motivated research into devices that measure the blood glucose concentration non-invasively, without breaking the skin barrier. One such device, described in U.S. Pat. No. 4,882,492 to Schlager, directs infrared light of two or more discrete wavelengths or within a continuous band into body tissue, either transmissively or reflectively. A microprocessor then calculates the glucose concentration from a series of such absorbance measurements. If the body tissue is well vascularized, such as a finger tip or ear lobe, then the resulting measurement of glucose approximates the blood glucose concentration. A major disadvantage of this approach however, is that other blood constituents have absorption spectra similar to that of glucose. As a result, it is difficult to obtain accurate measurements of blood glucose in real environments. A potential further disadvantage of this approach is that optical technologies may be expensive.

SUMMARY OF INVENTION

In accordance with the invention, apparatus and methods are provided for non-invasively measuring the concentration of a blood constituent on which an analysis can be performed (i.e., a blood analyte) in an individual. The blood analyte concentration is measured by applying a stimulus to an endogenous tissue with a stimulator, detecting a response to the stimulus with a detector, and correlating the detected response of the endogenous tissue to an analyte concentration with a correlator. Also provided is an optional occluding mechanism for obstructing a flow of blood to the stimulated and/or the responsive endogenous tissue. The measured analyte may be a physiological analyte, such as blood glucose, or a non-physiological analyte which affects the endogenous tissue, such as cocaine. The stimulated endogenous tissue may be the same tissue or a different tissue than the detected tissue.

In one embodiment, the stimulator includes at least two stimulation electrodes for applying an electrical stimulus to the endogenous tissue and the detector includes a detection electrode for detecting an electrical response of an endogenous tissue to the electrical stimulus to provide an electrical response signal. The apparatus further includes a controller for controlling the strength and duration of the electrical stimulus and for correlating the response signal to an analyte concentration of the user.

The apparatus may further include one or more input/output devices for facilitating user/monitor interaction. For example, in one embodiment, an alphanumeric display provides a visual indication of the blood analyte concentration to the user and a speaker provides an audible indication of the analyte concentration to the user. Also provided is a keyboard permitting user control of certain operations of the monitor.

Various arrangements for housing the stimulator and detector are possible. In one embodiment in which both the stimulated and detected endogenous tissue is the Median nerve, the stimulation electrodes and the occlusion mechanism are housed in a cuff adapted for securing to a finger of the user, adjacent to a first region of the nerve. The detector is housed in a wristband adapted for securing to the user's wrist at a location adjacent to a second region of the nerve.

With the present invention, apparatus and methods are provided for rapidly and reliably measuring blood analyte concentrations in individuals, such as glucose in diabetics. Moreover, these advantageous characteristics are achieved in a non-invasive manner (i.e., without breaking the skin barrier), thereby minimizing physical and emotional discomfort, the possibility of transmission of infectious material, and inconvenience to the user. The apparatus and methods described herein utilize analyte dependent alterations in the physiological or biochemical function of endogenous tissue to non-invasively measure analyte concentrations in humans. In a preferred embodiment for example, measurement of blood glucose in users relies on blood glucose dependent alterations in the electrophysiological function of peripheral nerves, such as the Median nerve. In essence, the apparatus and methods described herein employ a peripheral nerve as an endogenous glucose sensor. As such, this apparatus advantageously does not require placement of an artificial sensor within an individual or acquisition of a bodily fluid from the individual.

A further advantage of the present invention is that the measurement process does not require a disposable element. Consequently, the recurrent expense of test-strips is eliminated. The resulting reduced cost yields the added benefit of promoting frequent analyte measurement by individuals. A further advantage of the present invention is that readily available analog and digital electronic devices are used, thereby avoiding expensive components. Another advantage of the present invention is its ease of use. The software based controller minimizes the need for user expertise.

BRIEF DESCRIPTION OF THE DRAWINGS

The foregoing features of this invention, as well as the invention itself, may be more fully understood from the following detailed description of the invention in which:

FIG. 4 shows an illustrative cuff housing the stimulator and occlusion mechanism of the present invention;

FIG. 5 is a top view of an illustrative wristband housing the detector of the present invention;

FIG. 5A is a partial cross-sectional side view of the housing of FIG. 5;

FIG. 9 shows compound action potential waveforms in response to varying levels of stimulus.

DESCRIPTION OF THE PREFERRED EMBODIMENT

Figure 1:
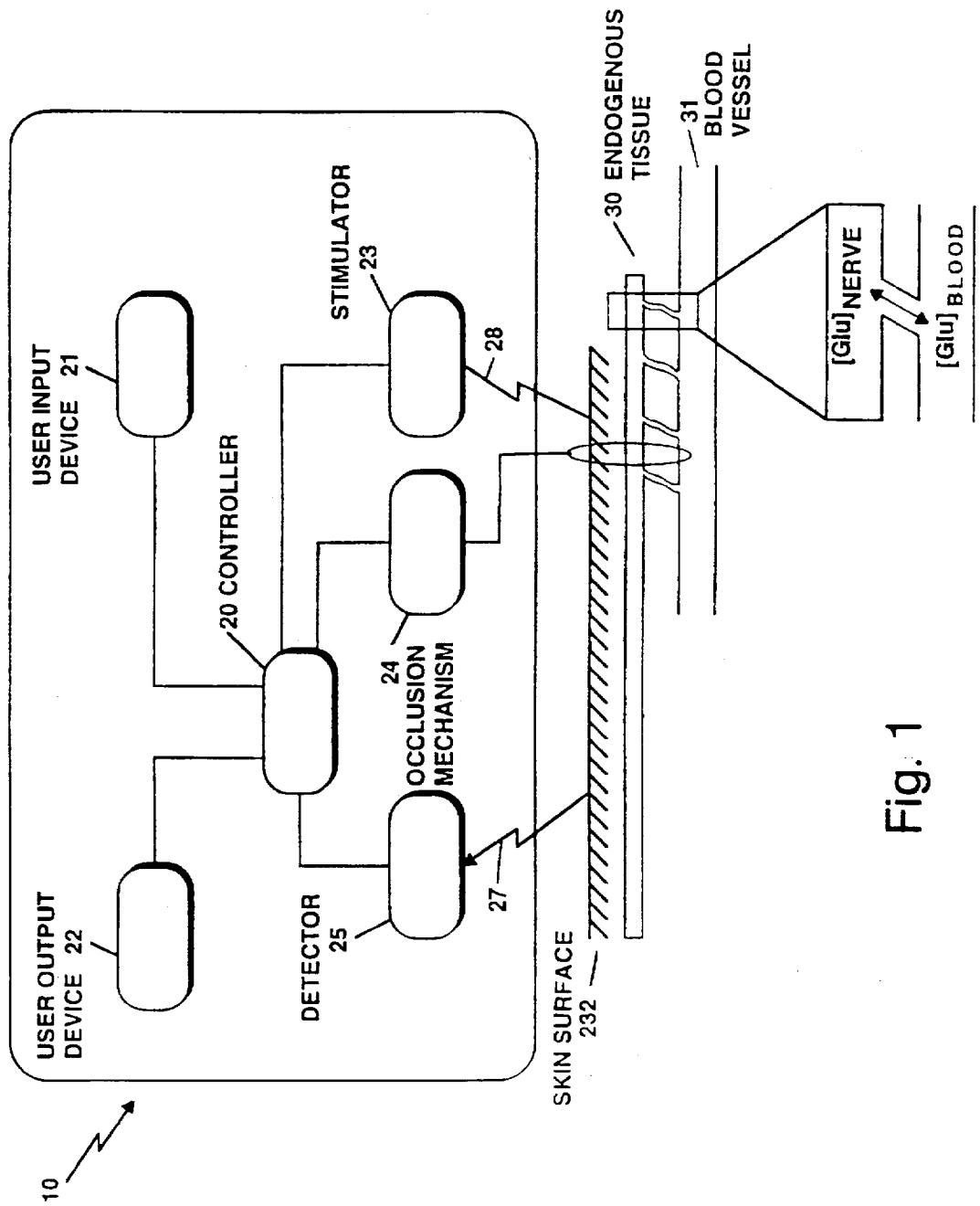
FIG. 1 is a block diagram of a non-invasive blood analyte measurement system in accordance with the invention.

Referring to FIG. 1, a blood analyte measuring system 10 for measuring the concentration of a blood analyte by communication with an endogenous tissue 30 of the user is shown. The analyte measuring system 10 includes a stimulator 23 for applying a stimulus 28 to an endogenous tissue 30 under the control of a controller 20. Also provided is a detector 25 which detects a response signal 27 of an endogenous tissue to the stimulus 28. A correlator correlates the detected response signal 27 of the endogenous tissue 30 to an analyte concentration of the user, as will be described, and an indicator is provided for indicating the analyte concentration in response to the correlation.

The measured blood analyte is any blood constituent on which an analysis can be performed and may be a physiological analyte, such as blood glucose, or a non-physiological analyte which affects the endogenous tissue, such as cocaine. The controller 20 is capable of executing stored instructions, generating and processing analog and digital signals, performing computations and storing data for subsequent retrieval and may take various forms, such as a microcontroller, as in the illustrative embodiment shown herein, or a personal computer.

The stimulus 28 may be applied to the same endogenous tissue from which the response signal 27 is detected. Alternatively however, the stimulus 28 may be applied to a first endogenous tissue and the response signal 27 detected at second endogenous tissue which is responsive to the stimulus.

In general, the endogenous tissue 30 is any tissue that is responsive to an applied stimulus 28 for producing a detectable response 27 as a function of an analyte concentration, such as certain nerves, muscle or other tissue. In the embodiment described herein, the endogenous tissue 30 is a nerve and the monitored blood analyte is glucose. Exemplary nerves for use in this manner are the Median nerve or the Ulnar nerve. It is observed that nerve glucose concentration is in a steady state relationship with the blood glucose concentration in a blood vessel 31 in communication with the nerve 30. When the nerve 30 is rendered hypoxic, it exhibits electrical activity commensurate with the concentration of glucose within the nerve (i.e. $[Glu]_{nerve}$). In particular, the response of the nerve 30 to an electrical stimulus 28 delivered to a hypoxic region of the nerve is characteristic of the nerve glucose concentration prior to initiation of hypoxia. By repetitive application of such stimulus and measurement of the associated nerve response, a highly accurate estimation of blood glucose concentration is provided.

More particularly, the utility of a peripheral nerve 30 as an endogenous blood glucose sensor and the non-invasive blood glucose measurement instrument described herein is based on several biological properties of peripheral nerves, including:

1. The concentration of glucose within peripheral nerves, called the endoneurial or nerve glucose concentration, is directly related to the blood glucose concentration.
2. Under hypoxic conditions (i.e. very low or absent supply of oxygen to a tissue), the electrophysiological function of a nerve is commensurate with the nerve glucose concentration.
3. The electrophysiological function of a peripheral nerve can be measured non-invasively.

Using the three aforementioned properties, a set of non-invasive electrophysiological measurements of a hypoxia peripheral nerve is translated into the individual's blood glucose concentration in a manner described below.

As noted above, the concentration of glucose within peripheral nerves is in a steady state with the blood glucose concentration. In other words, the nerve glucose concentration is directly proportional to the blood glucose concentration. In peripheral nerve, unlike most other tissues, this relationship is not significantly affected by insulin. Furthermore, changes in the blood glucose concentration effect similar changes in the nerve glucose concentration. Steady state is reestablished as quickly as ten minutes after an alteration in the blood glucose concentration. Consequently, a measurement of nerve glucose concentration is a reliable and relatively rapid indicator of blood glucose concentration.

Peripheral nerves are composed of tens of thousands of individual communication fibers called axons. The peripheral nervous system (PNS) in humans and most vertebrate animals requires a large amount of biochemical energy to maintain its normal function as a long distance signaling system. This energy is derived primarily from hydrolysis of phosphate groups on ubiquitous Adenosine tris-phosphate (ATP) molecules. Axons maintain their ATP supply through two biochemical processes: oxidative phosphorylation and glycolysis. These two processes predominate under different conditions and generate differing amounts of ATP and certain metabolic byproducts. In aerobic conditions, defined by the presence of sufficient oxygen, ATP is efficiently generated by oxidative phosphorylation through glucose breakdown and fatty acid degradation. In anaerobic conditions, defined by the absence of sufficient oxygen, ATP is inefficiently produced by the simple breakdown of glucose molecules. In addition, lactic acid is produced as a by-product of the process resulting in intracellular axonal acidification and hence a drop in axonal pH.

Anaerobic conditions can be externally imposed on peripheral nerves by occlusion of blood vessels through which oxygen and nutrients such as glucose are delivered. Occlusion is accomplished for superficial nerves of both the upper and lower extremities, by placement of an occlusion mechanism 24, such as a tourniquet 24, around an extremity such as the arm or a finger of the user. Use of a tourniquet 24 does not harm the nerve 30 or other tissues as long as the tourniquet is released within a reasonable period of time (e.g. 45 minutes).

The occlusion mechanism 24 compresses the tissue surrounding the blood vessel 31 that supplies oxygen and nutrients to the nerve 30 and may take various forms, such as the inflatable pneumatic cuff shown in FIGS. 2 and 4 and described below. The occlusion mechanism 24 is controlled by the controller 20 which determines the timing and duration of blood flow interruption according to a predetermined process.

Glycolysis is strictly dependent on the concentration of nerve glucose. Consequently, the ability of the axon to maintain ATP levels and prevent intracellular acidification during hypoxia depends on the nerve glucose concentration. Since the axon does not obtain additional glucose (or very little) during the hypoxic period, the efficiency of glycolysis during this period is dependent on the pre-hypoxic nerve glucose concentration. Furthermore, the electrophysiological properties of individual axons are altered by hypoxic decreases in ATP and pH, hence the electrophysiological properties of the nerve as a whole are affected in a parallel fashion.

Axonal fibers are impulse conducting tissues, where the impulses represent the essential signaling unit. In accordance with the present invention, the impulses, all-or-nothing electrochemical events called action potentials, are artificially initiated by electrical stimulation with stimulus 28. Thus, in the illustrative embodiment, the stimulus 28 is an electrical pulse stimulus applied by electrodes 77, 78 (FIG. 4). Other possible forms of stimulus 28, for stimulating a peripheral nerve 30 or more generally, for stimulating any stimulus responsive endogenous tissue, are magnetic stimulation, optical stimulation, other forms of electromagnetic energy stimulation (e.g. RF), sensory stimulation (e.g. vibration, temperature, or pressure), the application of an organic or inorganic chemical (e.g. sodium, neurotransmitter, anesthetic) or the application of a biological substance (e.g. protein, nucleic acids - DNA/RNA).

In the illustrative embodiment, the stimulator 23 comprises at least two stimulation, or stimulator electrodes 77, 78 (FIG. 4) in physical contact with the skin surface 32 immediately overlying the nerve 30 and a current generator. A current is passed between at least two, relatively closely spaced electrodes. The electrical pulse stimulus 28 may be a current pulse as in the illustrative embodiment, or a voltage pulse and is controlled by the controller 20 which determines the duration and magnitude of the stimulus 28 according to a predetermined process, as will be described below.

Although most of the current of stimulus 28 passes directly between the stimulator electrodes 77, 78 without entering the underlying nerve 30, a fraction will enter and stimulate the constituent axonal fibers. The number of fibers stimulated depends on the magnitude of the current as well as certain geometric and biophysical properties of the fibers. In general, the relationship between stimulation current and the number of activated axons is a sigmoidal function. Each stimulated axonal fiber generates a nearly simultaneous action potential that is propagated in both directions away from the point of stimulation.

Detector 25 detects a superimposed response signal 27 from all the stimulated axonal fibers, called the Compound Action Potential (CAP) and may take various forms. To this end, the detector 25 includes one or more detection electrodes in physical contact with the skin surface 32 immediately overlying the nerve 30, such as the illustrative two detector electrodes 85 in FIG. 5. The detector 25 may be positioned at the stimulation site or alternatively a short distance from the stimulation site. For example, in the case where the stimulated and detected endogenous tissue 30 are both provided by the Median nerve, the stimulator 23 may be positioned adjacent to a first region of the tissue, in a finger of the user, and the detector 25 may be positioned adjacent to a second region of the tissue, at the user's wrist, as shown in FIG. 2.

The amplitude of the compound action potential is a measure of the number of stimulated axonal fibers. As mentioned above, the electrophysiological properties of axons are altered by decreases in ATP concentration and pH. The most significant effect is an increase in the current required to stimulate an axon. Consequently, changes in ATP and pH are reflected in the amplitude and other parameters of the compound action potential. Since such changes are nerve glucose dependent during hypoxia, the compound action potential serves as a reporter on the nerve glucose concentration.

The detector 25 further includes electronic circuitry for amplifying and processing the response signal 27 (FIG. 6) and is connected to the controller 20 which interprets the response signal 27 by correlating the response signal 27 to an analyte concentration. For example, in the case of a glucose monitoring system 10, the controller 20 correlates certain features of the detected response signal 27 with blood glucose concentration on the basis of a predetermined function, as described below.

Once the response signal has been translated into a reading of the analyte concentration by the controller 20, this information is made available to the user by a user output device 22, such as an alphanumeric display providing a visual indication of the analyte concentration or a speaker providing an audible indication of the analyte concentration. Also provided are one or more user input devices 21 connected to the controller 20 to provide the user with a way of interacting with the monitor 10. An illustrative input device is a keyboard 37 (FIG. 2).

Figure 2:
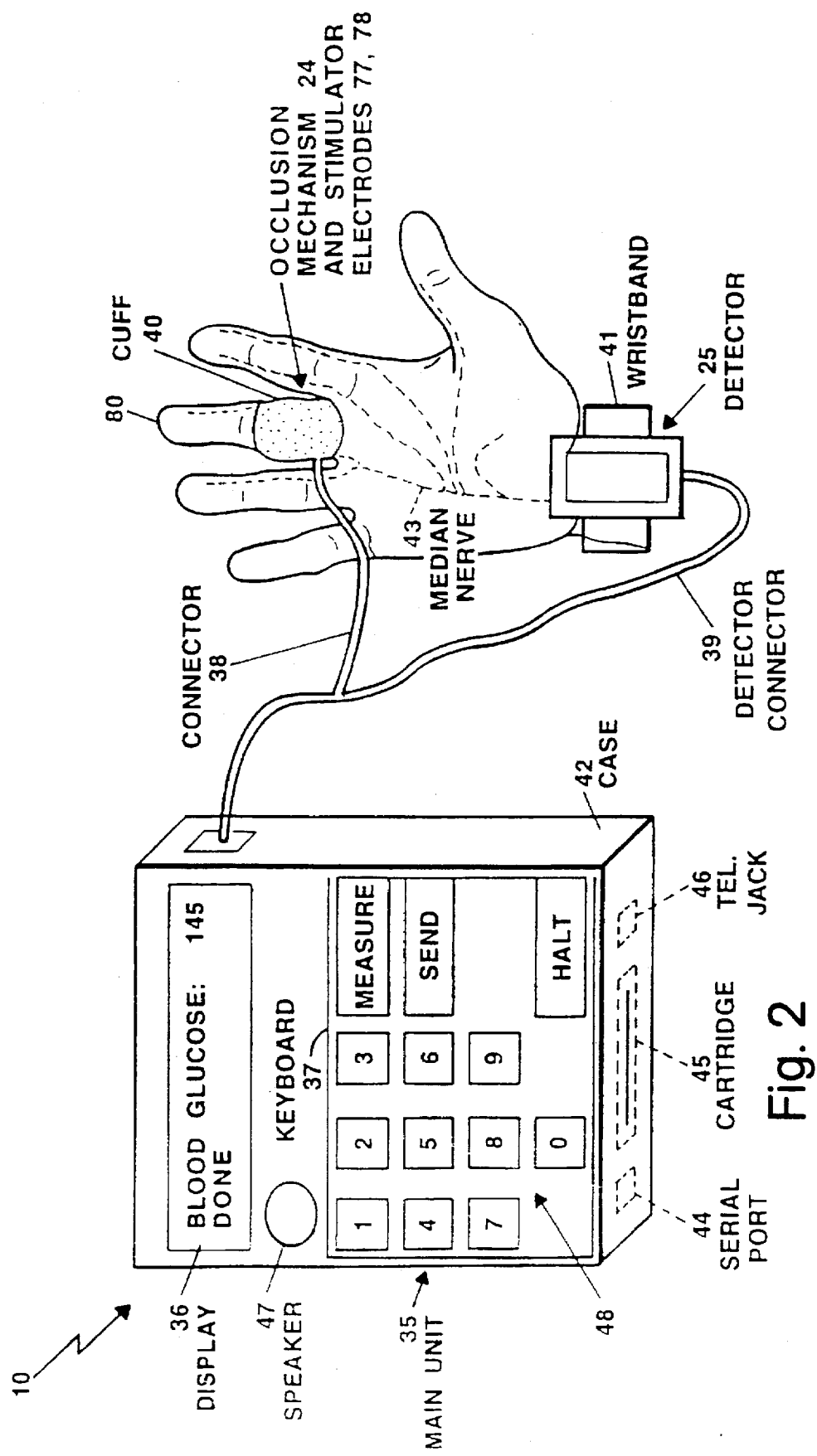
FIG. 2 is diagram of one embodiment of the analyte measurement system of FIG. 1.

Referring also to FIG. 2, one embodiment of the analyte measuring system, or monitor 10 utilizing the optional occlusion mechanism 24 is shown to include a main unit 35, a cuff 40, and a wristband 41. The cuff 40 houses the stimulator electrodes 77, 78 (FIG. 4) and the tourniquet 24 and the wristband 41 houses the detector 25. It will be appreciated that the stimulator 23, occlusion mechanism 24 and detector 25 may be physically arranged in many different ways. The essential constraint on any particular embodiment is that the stimulator electrodes 77, 78 (FIG. 4), tourniquet 24 and detector electrodes 85 (FIG. 5) contact the user at the appropriate anatomical location(s) to interact with the desired endogenous tissue(s). For example, alternatively, the stimulator electrodes 77, 78, tourniquet 24 and detector electrodes 85 may be housed within a rigid glove that conforms to the contour of the user's hand. This arrangement would place these components in the same anatomical relationship as shown in FIG. 2.

A further alternative arrangement for use in the monitor system 10 is to provide the stimulator electrodes 77, 78, tourniquet 24, and detector electrodes 85 all in a cuff, like cuff 40 of FIG. 2. In this case, the detection is performed directly adjacent to the stimulation site. Note that alternative embodiments, such as those in which a first endogenous tissue is stimulated and the response to such stimulation is detected in a second endogenous tissue, permit various other arrangements for positioning the stimulator electrodes 77, 78, tourniquet 24 and detector electrodes 85 relative to the user and which are within the spirit of this invention.

The main unit 35 includes user input devices 21 (FIG. 1), user output devices 22 (FIG. 1) and additional features which function as both input and/or output devices, all of which are referred to generally as user interface devices. One such input device is a keyboard 37 including a plurality of user actuable controls, which permits a user to input commands or messages to the main unit 25. The user actuable controls include alphanumeric keys 48 and command keys 49 for entering predetermined system commands, such as a MEASURE command key causing a calibration and measurement sequence to be performed, a SEND command key causing previously stored measurements to be sent to a remote location via a modem, and a HALT command key terminating the analyte measurement process, as will be described further in conjunction with FIGS. 7, 8A and 8B below. Braille elevations on the keyboard 37 can be included to assist visually impaired individuals.

A user output device 22 (FIG. 1) is provided in the form of a liquid crystal alphanumeric display 36 displaying the analyte concentration and other messages to the user. Another output device 22 is a speaker 47 which provides useful auditory feedback to individuals using the monitor 10, particularly those with visual disabilities.

Additional user interface devices extend the functional capabilities of the analyte concentration monitor 10. Specifically, a serial interface port 44 permits communication with a personal computer. A memory interface 45 for non-volatile memory cartridges enhances the data storage and software capabilities of the apparatus. A telephone jack 46 permits information to be transmitted over phone lines, thereby allowing automatic archiving of analyte measurements at remote computers and communication of the analyte measurements to medical personnel at remote locations.

Figure 6:
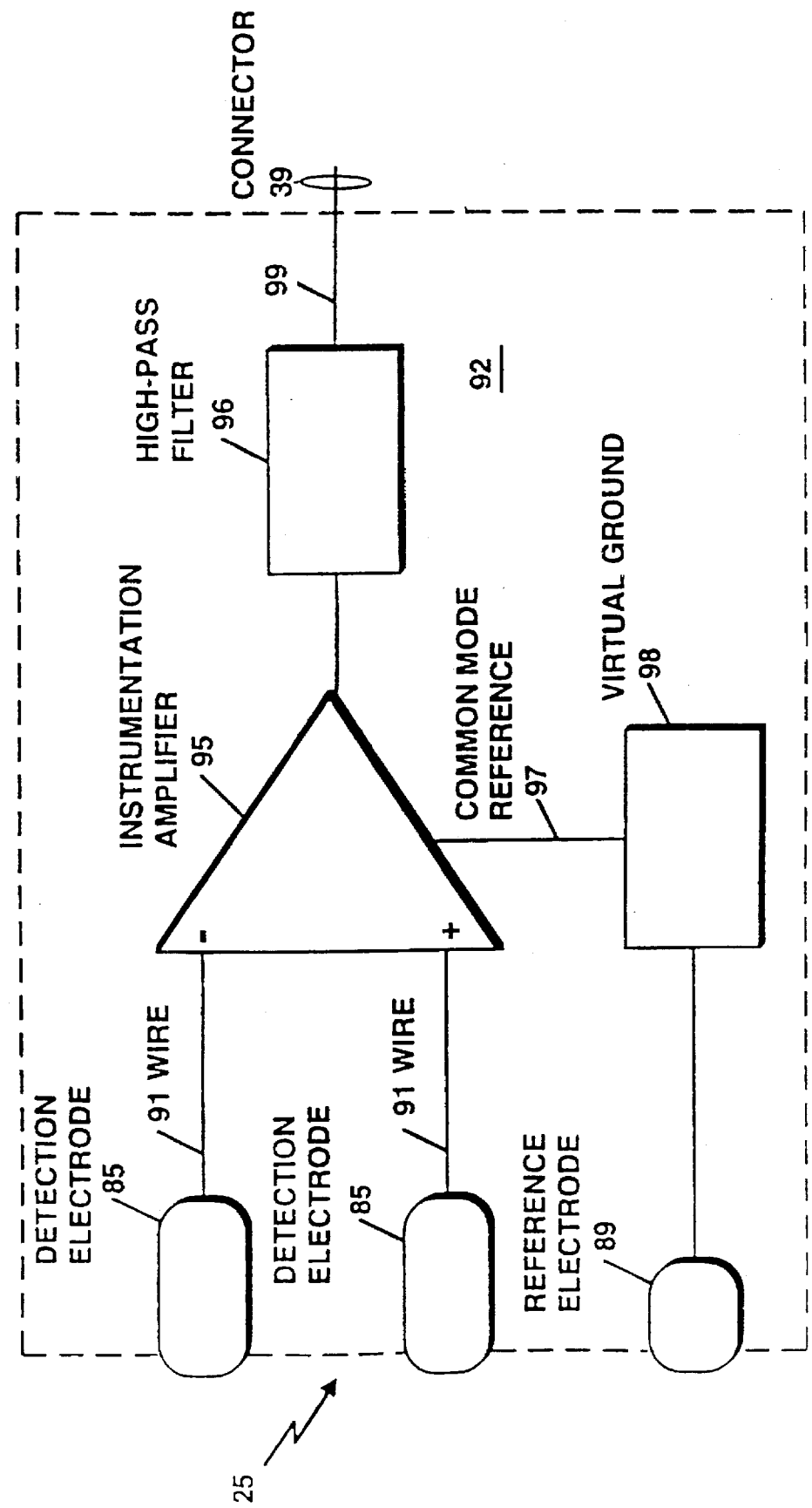
FIG. 6 is a schematic of the detector of the present invention.

The main unit 35 is housed within a box-like encasement 42. Two flexible connectors 38 and 39 connect the main unit 35 to the cuff 40 and the wristband 41, respectively. The cable 38 connecting the cuff 40 to the main unit 35 consists of a flexible, air-tight, rubber tube through which the tourniquet 24 is inflated and deflated with room air. Connector cable 38 also includes four insulated wires attached to the tube. These wires carry electrical stimulation current to stimulator electrodes 77, 78 (FIG. 4) located within the cuff 40 and carry a temperature signal from a temperature sensor 79 (FIG. 4) located within the cuff 40. Cable 39 connecting the detector 25 with the main unit 35 consists of a bundle of insulated wires. These wires provide a means to obtain the response signal 27 measured by the detector 25 and to provide electrical power to the electronic circuitry of the detector 25 within the wristband 41 (FIG. 6).

Figure 3:
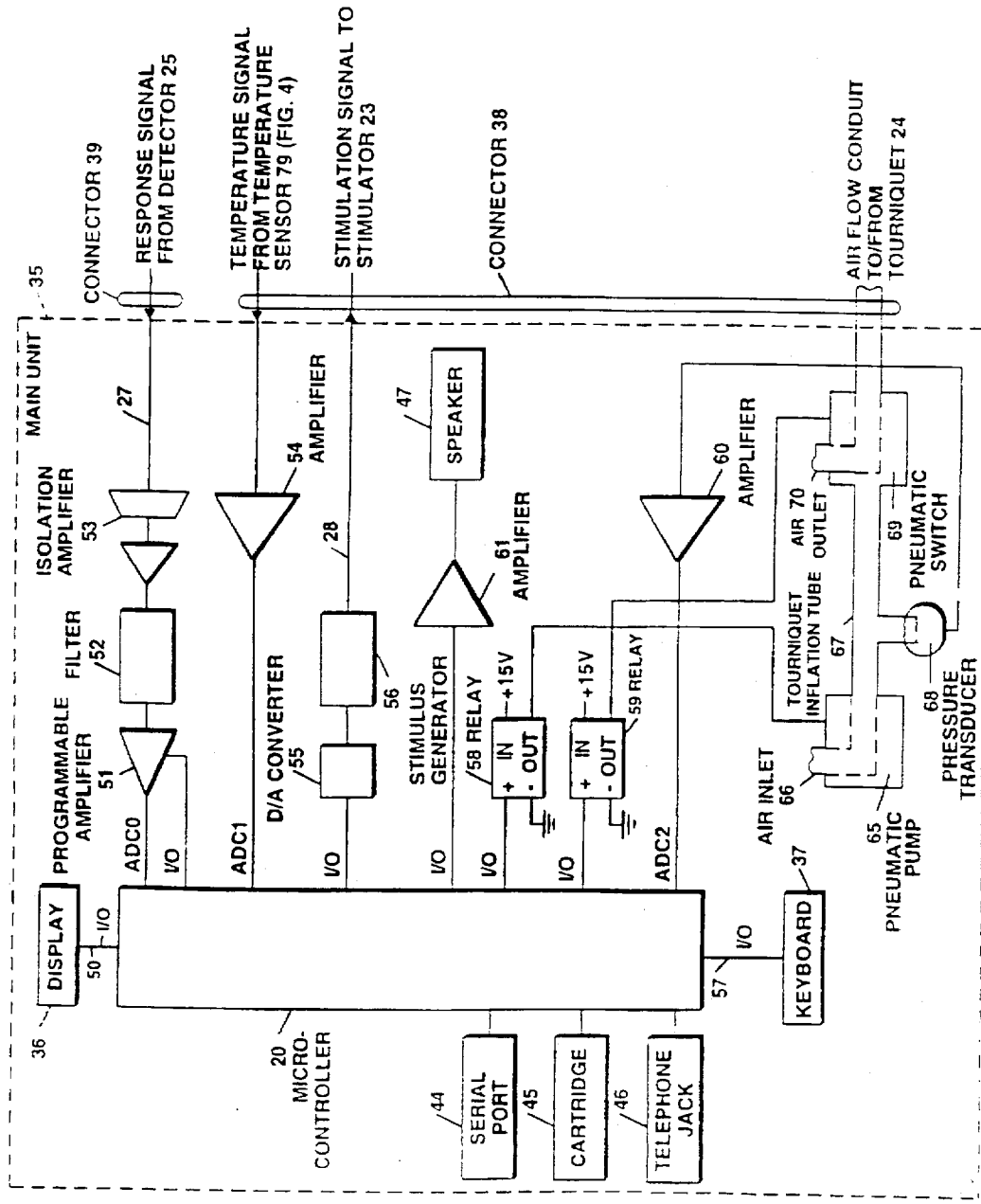
FIG. 3 is a schematic of the analyte measurement system of FIG. 2.

Referring also to FIG. 3, a schematic of the main unit 35 is shown. In the illustrative embodiment, the controller 20 is a single chip microcontroller, such as the Motorola M68HC16. Other microcontrollers, single or multiple chip, may alternatively be used. Preferably, the microcontroller 20 has random access memory, read only memory, multiple analog-to-digital converters and multiple input-output lines.

The microcontroller 20 operates in accordance with a software program stored in read only memory. This program carries out the analyte concentration measurement process, controls the user interface devices and executes diagnostic tests. The functionality supported by the microcontroller 20 may be extended by non-volatile add-on memory cartridges that plug into an interface cartridge slot 45 on the main unit 35.

The microcontroller 20 connects to the user interface devices, including the alphanumeric display 36, the keyboard 37 and the speaker 47. More particularly, the alphanumeric display 36 is connected to and controlled by a set of digital output signals 50 on the microcontroller 20. The contents of the display 36 are determined by the controller 20 which regulates the state of the digital output signals 50 on the microcontroller 20. Illustrative displayed messages include the blood glucose concentration and measurement status.

The keyboard 37 provides a set of digital input signals 57 to the microcontroller 20. The logic levels of these signals 57 corresponds to the particular keys depressed on the keyboard 37. The controller 20 determines which keys are depressed by monitoring the appropriate digital input signals 57.

One output signal of the microcontroller 20 serves as the input to an amplifier 61 which drives the speaker 47. The controller 20 generates tones of arbitrary frequency by oscillating the logic level on the output pin between low and high at the desired frequency.

The main unit 35 provides a means to control the air pressure within the tourniquet 24. In the preferred embodiment of the main unit 35, a pneumatic pump 65 elevates the pressure within a tube 67 that connects to the tourniquet 24 by pumping room air that enters from an inlet port 66. Power to the pneumatic pump 65 is controlled by a solid state relay 58 triggered by a single digital output line on the microcontroller 20. A pressure transducer 68 simultaneously detects the pressure within the inflation tube 67. This pressure is equivalent to the pressure within the tourniquet 24 and hence, the pressure compressing the user's finger. The transducer 68 generates an analog signal proportional to this pressure. This signal is amplified by a DC amplifier 60 and converted into a digital signal by an analog-to-digital converter on the microcontroller 20. The resulting digital signal is analyzed by the controller 20. A pneumatic switch 69 is controlled by a solid state relay 59 triggered by a single digital output line on the microcontroller 20. When the pneumatic switch 69 is opened, the pressure in the connection tube 67 and hence the tourniquet 24 is rapidly diverted through the switch 69 to the outside via an air outlet port 70. The controller 20 regulates the pressure in the tourniquet 24 by turning on the pneumatic pump 65 until the pressure in the tourniquet 24, as measured by the transducer 68, exceeds a predetermined set pressure. When the measurement period is finished or the operator depresses the HALT command key (FIG. 2), the controller 20 activates the output signal that selectively connects or disconnects the power to the pneumatic switch 69, thereby releasing tourniquet 24 pressure.

The main unit 35 processes a direct current analog signal generated by temperature sensor 79 (FIG. 4) in the cuff 40. The temperature signal is amplified by a DC amplifier 54 and then digitized by an analog-to-digital converter on the microcontroller 20. The resulting digital signal is analyzed by the controller 20.

A stimulus generator 56 generates a precise, load independent, low current signal 28 (FIG. 1) for electrically stimulating endogenous tissue 30 when passed through stimulator electrodes 77 and 78 (FIG. 4) located within the cuff 40. The stimulus generator 56 is capable of generating a 0.1 to 1000 millisecond current pulse of between zero and ten milliamps. The amplitude of the current pulse is controlled by an analog signal generated by a digital-to-analog converter 55, such as the Maxim MX7520, in response to digital signals from the microcontroller 20. The controller 20 regulates the pulse duration and amplitude of the stimulus 28 by setting the logic state of these output signals. The stimulus generator 56 has an output stage isolated from the main unit 35 power supply by an isolation amplifier (not shown). It will be appreciated that the stimulus generator 56 can be implemented in a number of different ways to achieve the aforementioned functionality. For example, a 3-terminal adjustable regulator, such as the Texas Instruments TL783C, can be used as an adjustable current source to provide the stimulus.

The main unit 35 receives a response signal from the detector 25 through connector 39. An isolation amplifier 53, such as the ISO100 optically coupled linear isolation amplifier from Burr-Brown, provides high voltage buffering between the main unit 35 and the detector 25 which is in physical contact with the user's skin. A bandpass filter 52, with a pass band from about twenty Hz to twenty Khz, rejects components of the response signal 27 outside the frequency range where signals from peripheral nerves are most readily detected. A programmable gain amplifier 51, with a gain programmable between approximately 10 and 500, provides a final stage of software controlled amplification prior to digitization by an analog-to-digital converter in the microcontroller 20. The gain of amplifier 51 is set by the logic level on output signals of the microcontroller 20. The gain is adjusted by the controller 20 so as to maintain the amplitude of the measured response signal 27 within the optimal digitization range of the microcontroller's analog-to-digital converter (e.g., ±5 volts).

Referring also to FIG. 4, an embodiment of cuff 40 (FIG. 2) housing the tourniquet 24 and stimulator electrodes 77, 78 is shown in connection with a user's finger 80. The tourniquet 24 is encased in a thin rigid plastic cylindrical encasement 75 and includes an elongated donut shaped bladder 76 composed of distensible and air-tight rubber capable of sustaining pressures up to 400 mmHg. The outer surface of the bladder 76 is attached to the inner surface of the encasement 75. Stimulator electrodes 77 and 78 and temperature sensor 79 are located on the inner surface of the bladder 76. In the illustrative embodiment, the stimulator electrodes 77 and 78 are thin circular discs of conductive non-corrosive material, such as platinum, iridium, or other metals or alloys. The size and shape of the stimulator electrodes 77 and 78 may vary depending on the dimensions of the user's finger 80 (e.g. adult verses child). In general, stimulator electrodes 77 and 78 have a diameter of about one centimeter. A single insulated wire passes through the inside of the bladder 76 to connect to the stimulator electrodes 77 and 78. These wires run through the connector 38 to the main unit 35 where they terminate at the stimulus generator 56. The temperature sensor 79 may be any device that generates a temperature dependent analog signal, such as the AD590 solid state temperature sensor from Analog Devices. Two wires connect the temperature sensor 79 to the connector 38 which is further connected to the main unit 35.

The bladder 76 is rapidly inflated with room air delivered through connector 38 from air inlet 66 located within the main unit 35 (FIG. 3). Because the cuff 40 is encased in a rigid material 75, the bladder 76 inflates inwardly causing compression of the user's finger 80. This inward bladder inflation has two consequences. First, as compression increases, the pressure within the finger 80 increases. When bladder pressure is sufficiently elevated, tissue pressure within finger 80 exceeds blood systolic pressure, thereby resulting in a temporary interruption of arterial blood flow to the compressed portion of the finger 80 and distally (i.e. towards the tip of the finger). Second, because the stimulator electrodes 77 and 78 and temperature sensor 79 are located on the inner surface of the bladder 76, inflation of the bladder ensures a tight apposition of these elements against the user's finger 80. However, the bladder 76 does not have to be inflated to its final pressure to enforce suitable contact between the electrodes 77 and 78 and the skin. Tight placement of the stimulator electrodes 77 and 78 against the finger 80 is important because it reduces the impedance of the electrode to skin contact, thus reducing the voltage that has to be developed across the electrodes in order to stimulate the underlying nerve 43 (FIG. 2). In addition, this arrangement minimizes variation in the electrode to skin impedance during the course of the measurement due to movement of the finger 80 which might otherwise degrade the quality of the analyte measurement.

Stimulator electrode 78 is the cathode 78 and serves as the active electrode and electrode 77 is the anode 77 and serves as the reference electrode. The reason for placing the cathode 78 proximally, as shown in FIG. 4, is that optimal nerve stimulation and recording is obtained when the active electrode is placed closest to the recording electrodes. In this apparatus, the recording electrodes 85 are located within the detector 25 located at the wrist. When a current, generated by the stimulus generator 56, is passed between the cathode 78 and anode 77, a portion passes through and stimulates the nerve 43 located beneath the electrodes 77 and 78.

Referring also to FIGS. 5 and 5A, alternate views of the wristband 41, are shown. Specifically, FIG. 5 shows a top view of the wristband 41 and FIG. 5A shows a side view, illustrating that the detector 25 housed therein is thin, giving the wristband an appearance similar to that of a watch. The wristband 41 consists of a plastic encasement 86 and a band 88. The encasement 86 serves as a support structure for the detector electrodes 85 and detection circuit 92. Detector electrodes 85 are strips of highly conductive, non-corrosive metal, such as platinum, iridium, or other metals or alloys. The exact dimensions of detector electrodes 85 depend on the physical dimensions of the user (e.g. adult vs. child or male vs. female). Each detector electrode 85 is connected by one wire 91 to the detection circuit 92 mounted on a circuit board within the wristband 41. The wire 91 is short, less then a few millimeters, and is insulated to minimize the acquisition of noise prior to buffering the response signal 27, as discussed below. The band 88 ensures a tight apposition of the detector electrodes 85 against the user's skin at the wrist. The ends of the band 88 are fitted with short VELCRO™ strips 87 that allow the band to be easily placed or removed. On one end of the band, a strip of conductive material 89 (e.g. platinum or iridium) is placed, which serves as a reference electrode. When the band 88 is placed around the wrist and secured by the VELCRO™ strips 87, the reference electrode 89 contacts the skin on the dorsal surface of the wrist, which is sufficiently distant from the nerve 43 (FIG. 2) to serve as a reference. The response signal output of the detector 25 is a buffered amplified analog signal representing the actual nerve signal and is sent to the main unit 35 via connector 39. Connector cable 39 also carries the power signal for powering the detector circuit 92.

Referring also to FIG. 6, a schematic of the detector 25, including detection circuit 92 and detector electrodes 85, is shown. The detection circuit 92 provides a means to buffer the high impedance electrode-to-skin contact and to preamplify the nerve response signal 27. The impedance of the skin-electrode interface is generally quite high. In many situations (e.g. EMG recording), the impedance is reduced by placing a conductive gel between the skin and the detector electrode. However, the apparatus described in this invention does not require such gels. In the present embodiment, the potential impedance problem is overcome by buffering the response signal 27 detected by the detector electrodes 85 a short distance from the actual detection site. Since the signals detected from sensory nerves are generally quite small, usually on the order of microvolts, it is advantageous to preamplify the response signals 27 prior to transmission to the main unit 35 in order to prevent degradation of the signal-to-noise ratio.

More particularly, detection circuit 92 includes an instrumentation amplifier 95 that generates an output signal proportional to the difference between the potential at the two detector electrodes 85. The detector electrodes 85 are connected to the instrumentation amplifier 95 by short insulated wires 91. Since the response signal 27 is in the microvolt range and the impedance of the electrode-skin contact very high, it is advantageous to use a FET-input instrumentation amplifier, such as the monolithic INA111 from Burr-Brown which has a very high input impedance ($>10^{12}$ ohms), a low bias current (<20 picoamps), and a common mode rejection ratio of about 115 decibels. An illustrative amplifier gain of approximately 1000 boosts the microvolt level response signal 27 detected at the electrodes 85 to the millivolt range, thereby reducing susceptibility to various forms of noise.

The output of the instrumentation amplifier 95 is filtered by a high pass filter 96 to remove the direct current component. A common mode reference 97 for the detector 25 is obtained by buffering the signal at the reference electrode 89 via a virtual ground circuit 98. The output of detector 25 is a processed response signal 99 transmitted to the main unit 35, where it is isolated by isolation amplifier 53 (FIG. 3). Power for the detector 25 is provided by an isolated power supply located within the main unit 35. Thus, the detector 25 is electrically isolated from external power sources to the main unit 35.

OPERATION OF INVENTION

Figure 7:
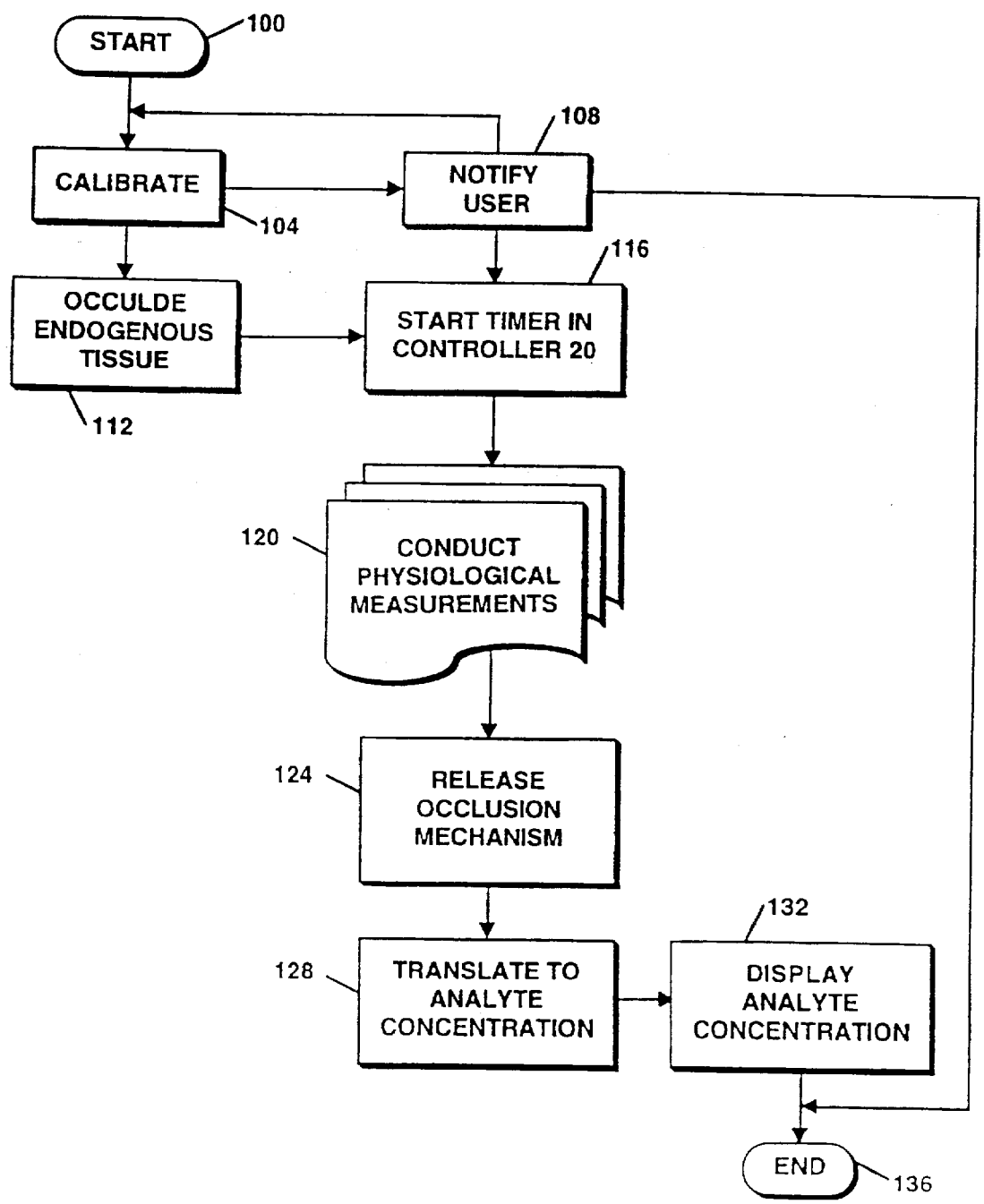
FIG. 7 is a flow diagram of a blood analyte measurement process.

Referring also to FIG. 7, the multi-step operation of monitor 10 will now be described. Operation of the monitor 10 is commenced in step 100 by positioning the apparatus in the appropriate anatomical location(s) on the user. In the illustrative embodiment of FIG. 2, in which the Median nerve 43 serves as an endogenous glucose sensor, the middle (3rd digit) or index (2nd digit) finger is placed within the cuff 40 as shown in FIGS. 2 and 4. The signal-to-noise ratio is maximized by observing the following two positioning principles. First, the cuff 40 is placed as proximally as possible to the base of the finger, as opposed to the tip. Second, the ventral aspect of the finger contacts the stimulator electrodes 77 and 78 as shown in FIG. 4. The wristband 41 is secured at the wrist by apposing the two VELCRO™ strips 87 on either end of the band 88. In the preferred embodiment, the wristband 41 is positioned at the mid line portion of the wrist, thereby maximizing the detected response signal 27. Note that alternatively, the Ulnar nerve could be used to measure blood glucose by placing the cuff 40 over the 4th or 5th digits and positioning the wristband 41 in a medial location. Other peripheral nerves, such as those in the lower extremities, may be used in individuals for which the upper extremities are inappropriate or inaccessible. Thereafter, the monitor 10 is powered.

The user initiates operation of the monitor 10 in step 100 by actuating an appropriate key, such as the MEASURE command key on the keyboard 37 of the main unit 35 (FIG. 2). The monitor 10 must be calibrated prior to each use. This operation is performed at the time of an analyte measurement initiated by user actuation of the MEASURE command key.

The calibration sequence is carried out in step 104. The purpose of calibration is to determine an optimum stimulus. For example, in the blood glucose monitor embodiment, the calibration step 104 includes stimulating a nerve several times with stimuli of different amplitudes and determining, in response to the detected nerve signals, a stimulus amplitude capable of evoking a maximum nerve signal response, as described below in conjunction with FIGS. 8A, 8B and 9.

If the calibration process in step 104 is unsuccessful, for example, if the signal-to-noise ratio associated with the detected response signal 27 is to too low to determine an optimum stimulus amplitude, then the user is notified of this condition in step 108. Such an error condition might occur in the case of attempting to detect a response signal from a severely diseased nerve. Thereafter, in response to a user actuated command, the calibration step 104 may be repeated (i.e., by user actuation of the MEASURE command key) or alternatively, the monitor operation may be terminated (i.e., by user actuation of the HALT command key).

Once calibration has been successfully completed, an optional step 112 may be performed in which the stimulated and/or detected endogenous tissue is rendered hypoxic by occluding the flow of blood to the tissue. In the illustrative blood glucose monitor embodiment, this step entails inflating the tourniquet 24 in the cuff 40. Inflation of the tourniquet 24 is achieved as described above, by actuation of the relay 58 by the controller 20 (FIG. 3). Recall that in response to actuation of relay 58, room air is pumped into the tube 67 that connects to the tourniquet 24, thereby inflating the tourniquet to interrupt the flow of blood to the nerve 43 (FIG. 2) and to ensure that the stimulator electrodes 77, 78 (FIG. 4) remain in stable contact with the user's finger.

In step 116, a timer associated with the controller 20 (FIG. 1) is initialized. The timer determines the timing of the various steps of the analyte measurement procedure in subsequent step 120. For example, the timer determines how long the stimulated endogenous tissue is maintained hypoxic, the duration of application of a stimulus to the endogenous tissue, the timing of the detection of the response of the endogenous tissue to the applied stimulus, etc.

Thereafter, in process step 120, analyte measurements are conducted. More particularly, step 120 includes multiple sub-steps of applying a stimulus having characteristics determined during calibration to an endogenous tissue for a predetermined duration, detecting a response signal of the stimulated, or other, endogenous tissue to the stimulus, and repeating the stimulating and detecting steps at a predetermined repetition rate for a predetermined duration. Additionally, the detected response signals, or parameters representing these signals, are stored for later use by the monitor. In step 124, the occlusion mechanism is released, thereby restoring the flow of blood to the stimulated and/or responsive endogenous tissue.

Once the occlusion mechanism is released, the monitor 10 translates the detected response signals into an analyte concentration in step 128. This step includes various sub-steps, such as normalization of a vector including extracted parameters of the detected response signals and multiplication of a normalized vector by vector correlation coefficients, as described in conjunction with the process for translating nerve response signals into glucose concentration of FIGS. 8A and 8B.

Finally, the analyte concentration thus determined is displayed to the user in step 132. This display may be achieved with the use of an alphanumeric display, such as the display 36 shown in FIG. 2, or with a speaker 47 to provide an audible indication of the measured analyte. Furthermore, the display provided in step 132 may be a remote display, such as a display to a physician at a remote location via a modem and telephone jack 46 (FIG. 2). Or, the display of step 132 may be a delayed display provided to either the user or the physician at some time after the monitor 10 has carried out the measurement process, such as may be achieved by storing the measured analyte concentration in memory associated with the main unit 35 or in the memory of a personal computer in communication with the main unit 35 via the serial port 44 of FIG. 2. The operation of analyte monitor 10 is terminated in step 136, as shown.

Figure 8A:
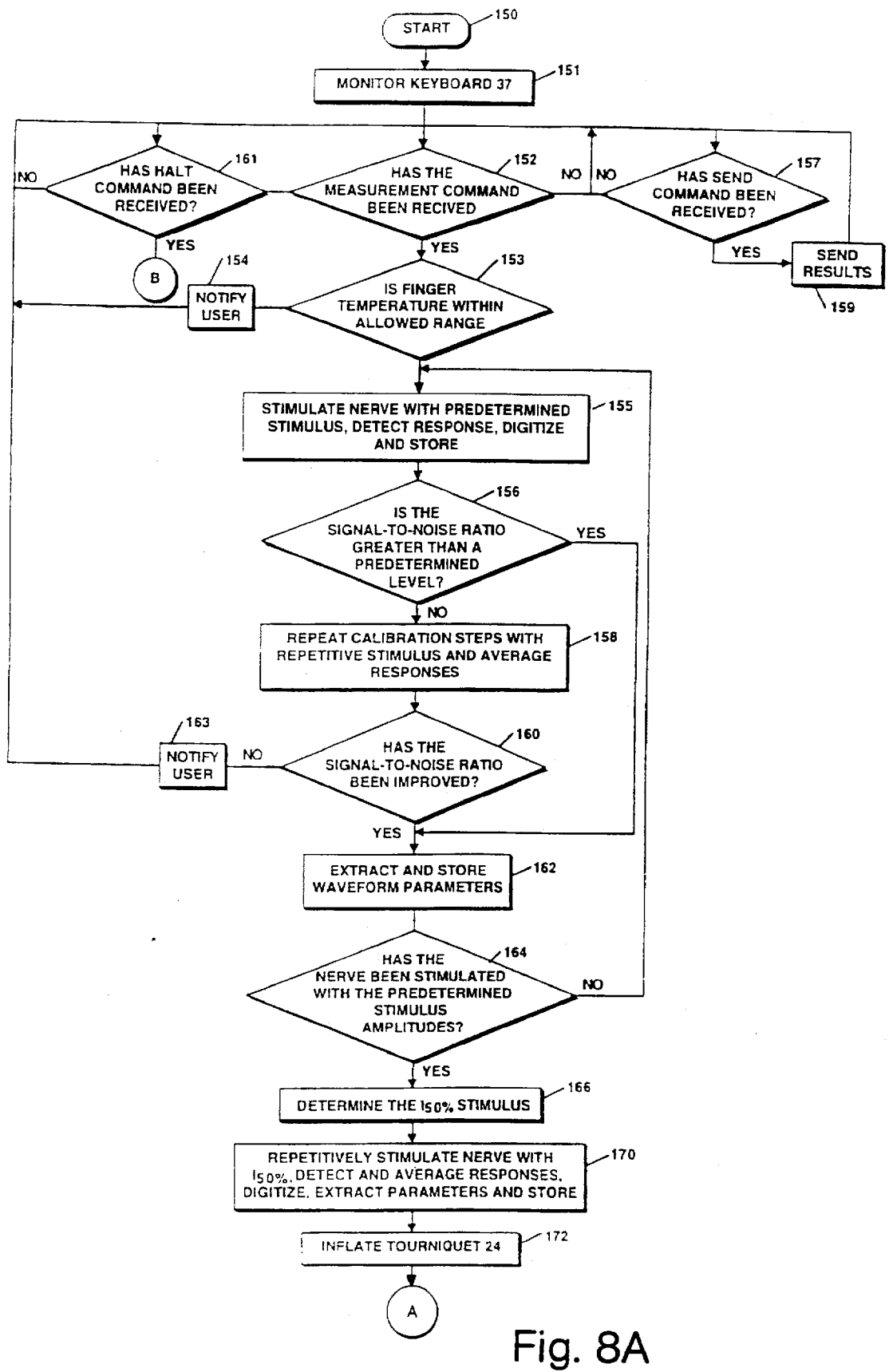
FIG. 8A is a first portion of a flow diagram of a blood glucose measurement process.
Figure 8B:
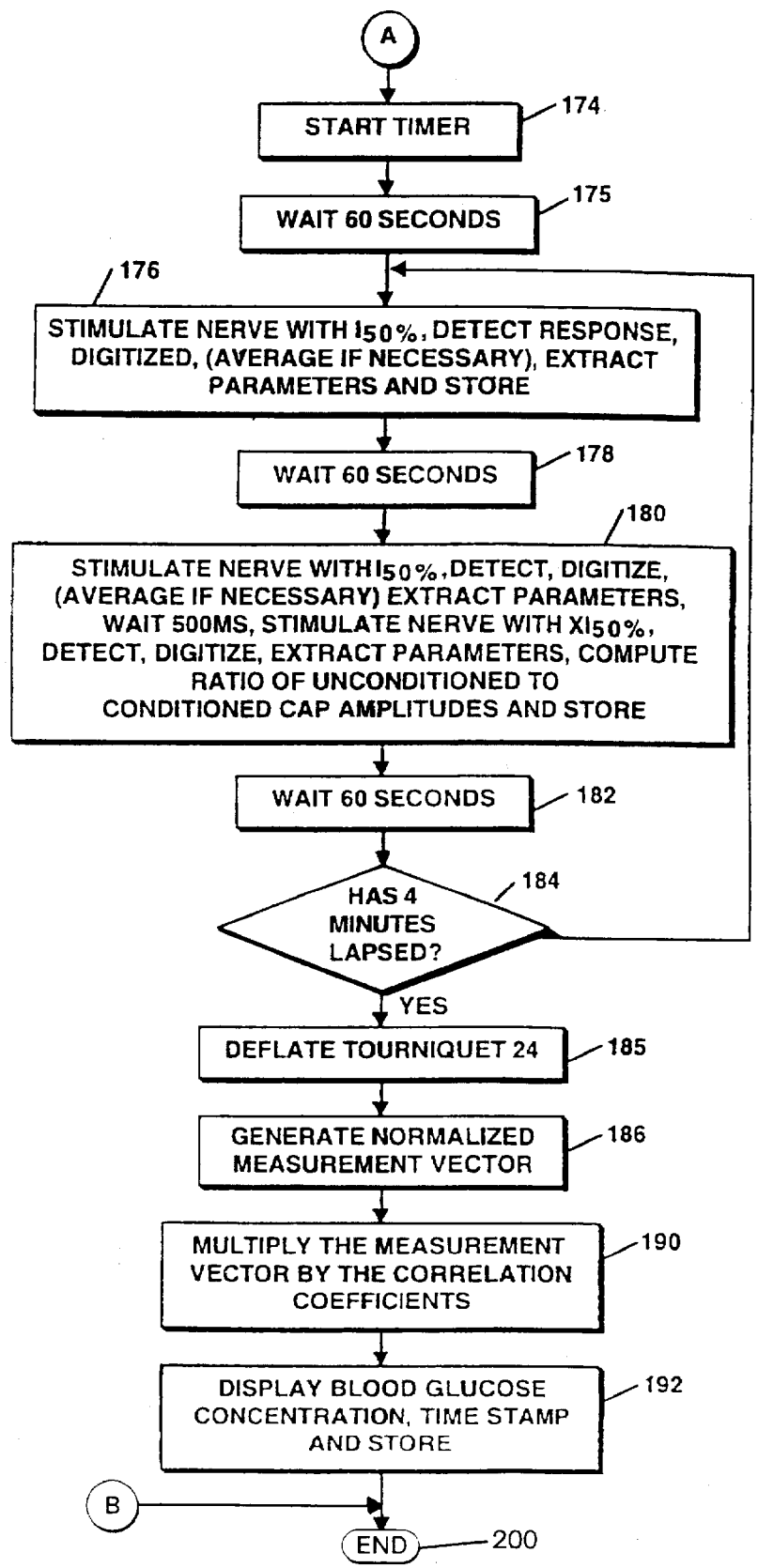
FIG. 8B is a second portion of the flow diagram of FIG. 8A.

Referring to FIGS. 8A and 8B, an illustrative flow diagram for the operation of the blood glucose monitor 10 described above is shown. The process commences in step 150, by placing the cuff 40 and the wristband 41 (FIG. 2) at the appropriate anatomical locations on the user, as described above. Thereafter, the keyboard 37 (FIG. 2) is monitored by the controller 20 in step 151.

In step 161, it is determined whether the HALT command has been received. Actuation of the HALT command key of the keyboard 37 (FIG. 2) at any time during operation of the monitor 10 causes the monitor operation to be interrupted and terminated by proceeding to step 200 (FIG. 8B). In step 157, it is determined whether the SEND command key has been received. Actuation of the SEND command at any time during operation of the monitor 10 causes previously stored measurements to be sent to a remote location via telephone jack 46 and a modem.

In step 152, it is determined whether a MEASURE command has been received in response to actuation of the MEASURE command key of the keyboard 37 in FIG. 2. If it is determined that the MEASURE command has been received, then monitor 10 checks the finger temperature in step 153. If the temperature is not within acceptable limits (e.g., within several degrees of room temperature), then the user is notified in step 154 and the keyboard 37 is monitored for actuation by the user in step 151. If in step 153 it is determined that the temperature is within acceptable limits, then the monitor 10 performs the calibration process in steps 155-166. Specifically, in step 155, the nerve, such as the Median nerve 43 of FIG. 2, is stimulated with a stimulus 28 (FIG. 1), a response signal 27 of the Median nerve 43 to the applied simulation is detected, and the response signal 27 is digitized and stored. More particularly, the stimulus generator 56 (FIG. 3) generates a stimulus signal 28 in response to digital signals from the controller 20, as described above. The stimulus signal 28 is transmitted to the stimulator electrodes 77, 78 (FIG. 4) via connector 38. One illustrative stimulus signal is a pulsed current waveform having a duration of approximately two-hundred microseconds. The amplitude of the stimulus signal is initialized to a predetermined value, such as three milliamps.

The response signal 27 generated by the Median nerve 43 in response to the applied stimulus signal 28 is detected by detector electrodes 85 (FIGS. 5 and 5A) and is referred to as a compound action potential (CAP). FIG. 9 shows an illustrative CAP 210 detected in response to a 3.3 milliamp stimulus signal 212. The detected CAP 210 is digitized and stored in a dedicated region of random access memory by the microcontroller 20 (FIG. 3).

In process step 156, it is determined whether the detected CAP 210 has a signal-to-noise ratio greater than a predetermined level. As noted above, in some circumstances (e.g. diseased nerve), the evoked CAP has a poor signal to noise ratio. If the CAP signal-to-noise ratio is less than a predetermined level, then the nerve is stimulated repetitively in step 158. More particularly, in step 158, the nerve is stimulated at a rate of approximately two to four stimuli per second with the identical stimulus for a predetermined duration. The detected CAP responses evoked by the repetitive stimuli are then averaged to provide an average CAP which is digitized and has parameters extracted therefrom which are stored as described below in conjunction with step 162.

If the procedure of step 158 does not improve the signal-to-noise ratio of the detected CAP to a suitable level, then an error message is presented to the operator by any available output device, such as the alphanumeric display 36, in step 163. Thereafter, the keyboard 37 is monitored for actuation by the user in step 151. For example, the user may choose to retry the calibration procedure by depressing the MEASURE command key again.

In the event that it is determined in step 156 that the signal-to-noise ratio of the detected CAP is acceptable (i.e., whether acceptable initially or improved in process step 158), then process step 162 is next performed in which the microcontroller 20 extracts predetermined signal parameters from the digitized CAP waveforms and stores such parameters. Exemplary extracted and stored waveform parameters are the peak to peak amplitude of the CAP (i.e., the difference between the amplitude at the maximum and minimum points), the total area underneath the CAP, the width of the CAP, and the latency of the CAP (i.e., the interval between application of the stimulus signal to the nerve and the appearance of the CAP). The extracted parameters are stored in memory associated with the microcontroller 20.

Process step 164 is next performed in which it is determined whether the stimulated nerve has been stimulated with a predetermined number of stimuli of different amplitudes. If the nerve has not been stimulated by the predetermined stimuli, then process step 155 is repeated with a different stimulus amplitude. The CAP 218 evoked thereby is shown in FIG. 9. In the illustrative blood glucose measurement process, the predetermined number of stimuli applied to the nerve during calibration is three, with respective amplitudes of 3.3, 3.8 and 5 milliamps. Thus, in step 164, it is determined that the nerve has not been stimulated by the three stimuli and step 155 is repeated in which the nerve is stimulated with a stimulus signal 216 having an amplitude of 3.8 milliamps, resulting in a CAP 218 that is then digitized and parameters thereof are stored. After the second time that step 164 is performed, process step 155 is repeated for a third time, during which a stimulus signal 222 having an amplitude of 5 milliamps is applied to the nerve and the detected CAP 224 is digitized and stored by the microcontroller 20. Preferably, stimulation of the nerve with the three increasing amplitude stimulation signals 212, 216 and 222 (i.e., repetition of step 155) is performed at increments of approximately every five to ten seconds.

Once the nerve has been stimulated with the predetermined number of stimuli of different amplitudes and the CAPs evoked thereby have been processed to provide parameters which are stored, then process step 166 is performed in which an optimum stimulus amplitude is determined. More particularly, the magnitude of the electrical stimulus signal that evokes a CAP that is approximately fifty percent of the maximum evocable CAP is determined. This stimulus signal is referred to as the $I_{50\%}$ stimulus signal and is used as a standard stimulus for performing measurements of analyte concentration. Although other fractions of the maximum evocable CAP may be used to provide the optimum stimulus signal, 50% is selected since relatively small changes in the electrophysiological properties of peripheral nerves cause large changes in the CAP evoked by the $I_{50\%}$ stimulus signal.

The maximal evocable CAP is obtained when the peak to peak amplitude ceases to increase, despite increasing stimulus magnitude. It is possible to estimate this value without actually using maximal stimuli (which may be uncomfortable for the user) by extrapolating CAP peak to peak amplitudes from sub-maximal stimuli, such as the 3.3 milliamp, 3.8 milliamp and 5 milliamp stimulus signals 212, 216 and 222, respectively. Once the maximal CAP peak to peak amplitude is obtained, the 50% amplitude and its associated stimulus (i.e., the $I_{50\%}$ stimulus) are readily determined by interpolating among the measured values.

Process step 170 is next performed in which the CAP peak to peak amplitude evoked by the $I_{50\%}$ signal is measured by repetitively applying the $I_{50\%}$ stimulus signal to the nerve at a rate of approximately two to four stimuli per second for a predetermined duration with stimulator electrodes 77, 78 (FIG. 4) and detecting the CAP response signal with detector electrodes 85 (FIGS. 5 and 5A). Also in step 170, the CAP response signals thus detected are digitized and averaged. Finally, parameters of the average waveform are extracted and stored as described above in conjunction with process step 162 for latter use in normalizing measurements. More particularly, the magnitude of subsequent response signals are represented as a fraction of the response detected in step 170.

Once the $I_{50\%}$ stimulus signal and response are determined and stored in steps 166 and 170, respectively, calibration is completed and the monitor 10 proceeds with measurement of the user's blood glucose concentration. To this end, step 172 is next performed, in which the nerve 43 (FIG. 2) is rendered hypoxic by rapid inflation of the tourniquet 24. The tourniquet pressure required to interrupt blood flow is predetermined, according to published functions that relate this pressure to the width of the tourniquet 24, the diameter of the user's finger and the user's systolic blood pressure, as described in an article entitled "The digital tourniquet: How safe is it?" by J. D. Lubahn, J. Koeneman and K. Kosar in the *Journal of Hand Surgery*, 5:664–669 (1984) and an article entitled "New finger cuffs for use with digital tourniquets" by J. A. McEwen, P. T. Gropper and R. W. McGraw in the *Journal of Hand Surgery*, 6:888–892 (1988), both of which are incorporated herein by reference.

When the predetermined pressure set point is reached in the tourniquet 24, the microcontroller timer is initialized in step 174. The application of subsequent electrical stimuli and nerve signal measurements are temporally scheduled according to this timer.

During the few minutes that the tourniquet 40 is inflated and the nerve is rendered hypoxic, a set of electrophysiological measurements of nerve function are obtained, in steps 176–184. Prior to the first measurement, sixty seconds are permitted to lapse in step 175 to permit hypoxia to take effect. In process step 176, the CAP peak to peak amplitude evoked by the $I_{50\%}$ signal during hypoxia is measured by applying the $I_{50\%}$ stimulus signal to the nerve with stimulator electrodes 77, 78 (FIG. 4) and detecting the CAP response signal with detector electrodes 85 (FIGS. 5 and 5A). Also in step 176, the CAP response signal thus detected is digitized. If the signal to noise ratio of the CAP thus obtained is low, then the nerve is stimulated at a rate of approximately two to four stimuli per second with the identical stimulus for a predetermined duration. The detected CAP responses evoked by the repetitive stimuli are then averaged to provide an average CAP which is digitized. Finally, the parameters are extracted from the single or averaged CAP and stored, as described above in conjunction with process step 162.

Figure 10:
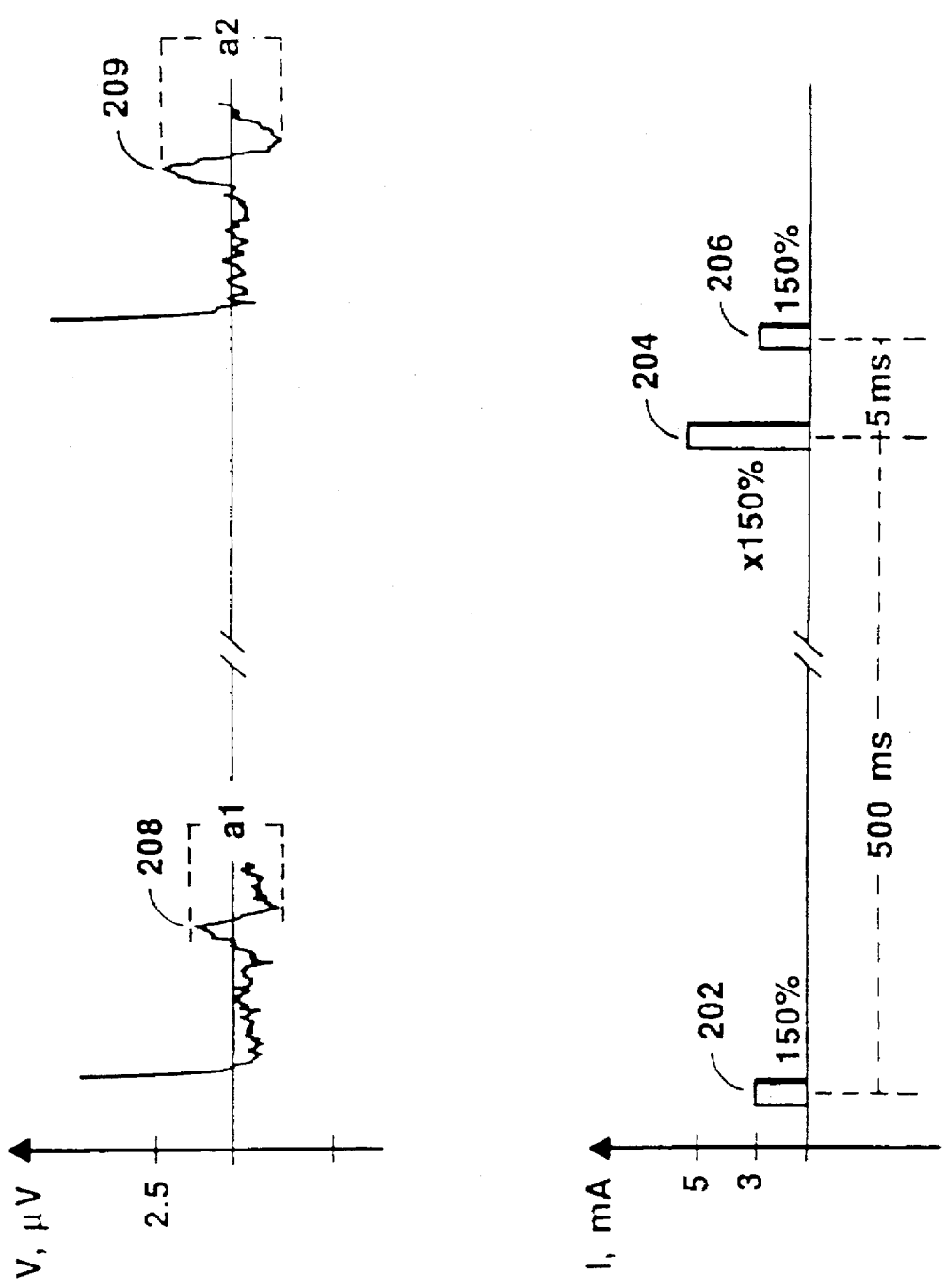
FIG. 10 shows a conditioned compound action potential waveform.

In subsequent step 178, sixty seconds are permitted to lapse, following which a conditioned CAP (i.e., the ratio of an unconditioned to a conditioned CAP amplitude) is detected in step 180. Referring also to FIG. 10, this ratio is obtained by applying the $I_{50\%}$ stimulus 202 to the nerve, followed by the application of a conditioning stimulus 204 having a magnitude of between approximately 1.5 and 5.0 times the $I_{50\%}$ stimulus after approximately 500 milliseconds, and another $I_{50\%}$ stimulus signal 206 following the conditioning stimulus 204 by approximately five milliseconds, as shown. The CAP resulting from the first $I_{50\%}$ stimulus 202 is labelled 208 and the CAP resulting from stimuli 204 and 206 is labelled 209. If the signal to noise ratio of either the unconditioned CAP or conditioned CAP is low, then the same sequence of three stimuli is repeated at a rate of approximately once per second for a predetermined duration. The detected unconditioned and conditioned CAP responses evoked by the repetitive stimuli are then averaged to provide an average unconditioned CAP and conditioned CAP. The single or averaged unconditioned CAP 208 has a peak to peak amplitude labeled $a_1$ and the single or averaged conditioned CAP 209 has a peak to peak amplitude labeled $a_2$. The unconditioned to the conditioned CAP ratio determined in step 180 is thus, given by $a_1/a_2$. Also in process step 180, this ratio is stored.

In the preferred process for determining the blood glucose concentration, the measurements of steps 176 and 180 are alternatively taken every 60 seconds for 4 minutes. To this end, after the unconditioned to conditioned CAP ratio is obtained in step 180, sixty seconds are permitted to lapse in step 182. Thereafter, in process step 184, it is determined whether four minutes has lapsed since the timer was initialized in step 174. If four minutes has lapsed, then the CAP measurements are completed and the results are thereafter processed to correlate to the user's blood glucose concentration in steps 186–190. Alternatively, if four minutes has not lapsed, then process steps 176–182 are repeated. It will be appreciated by those of skill in the art that the measurement process described herein may be readily varied, for example by varying the inter-measurement interval (e.g. to take measurements every 45 or 90 seconds, as opposed to the illustrative 60 second intervals), by varying the measurement durations (e.g. to durations of 2 or 5 minutes, as opposed to the illustrative 4 minutes) and by taking other types of measurements (e.g. by using other than the $I_{50\%}$ stimulus signal and/or conditioned CAP process). Thus, modifications to the illustrative process are contemplated and are within the scope of this invention.

Once it is determined in step 184 that four minutes has lapsed, thereby indicating that the measurements have been finished, the tourniquet 24 is rapidly deflated in process step 185. This is achieved by actuation of the release relay 59 (FIG. 3) by the microcontroller 20 which causes air in the tourniquet 24 to be released through outlet 70.

Thereafter, in steps 186 and 190, the ensemble of electrophysiological nerve measurements are translated into a blood glucose concentration by the microcontroller 20 with the use of a correlation function in order to determine the blood glucose concentration of the user. In step 186, a measurement vector "m" is generated, including one or more extracted parameters generated from the detected $I_{50}\%$ CAP waveform and the conditioned CAP waveforms in steps 176 and 180, respectively. The measurement vector "m" represents a temporal sampling of nerve function during hypoxia. The measurement vector resulting from the above described measurement process is thus, comprised of four specific measurements, as shown in equation (1):

$$m=\{a_{60}, a_{180}, b_{120}, b_{240}\} \tag{1}$$

The timing of each measurement, in seconds, is designated as a subscript. For example, $a_{180}$ represents the amplitude of the $I_{50\%}$ CAP response 3 minutes after initiation of hypoxia and $b_{120}$ represents the ratio of the unconditioned to conditioned $I_{50\%}$ CAP response two minutes after initiation of hypoxia. Note that although the measurement vector is described herein as containing the amplitude of detected CAP responses, other CAP parameters such as latency and/or width may also be used to provide the measurement vector.

The elements of the measurement vector which represent absolute measures of nerve function (e.g., CAP in response to an the $I_{50\%}$ stimulus) are normalized in order to minimize the natural variability in peripheral nerve function among individuals or changes that might occur within specific individuals over time (such as those due to aging), providing the normalized measurement vector shown in equation (2):

$$\tilde{m}=N(m) \tag{2}$$

where N represents the overall normalization function. The specific normalization procedure depends on the particular type of measurement. For example, CAP peak to peak amplitudes in response to the $I_{50\%}$ stimulus signal during hypoxia (i.e. $\{a_{60}, a_{180}\}$) are divided by the peak to peak amplitude of the pre-hypoxic $I_{50\%}$ response (obtained in process step 170) to arrive at relative values (i.e. $\{\tilde{a}_{60}, \tilde{a}_{180}\}$). The unconditioned to conditioned CAP ratios (i.e., $\{b_{120}, b_{240}\}$) are relative values and thus, do not require normalization.

The vector of normalized measurements, $\tilde{m}$, is translated into a blood glucose concentration in accordance with a function, F, as shown in equation (3):

$$[glucose]_{blood}=F(\tilde{m}_{preferred}) \tag{3}$$

The function, F, may be a linear or non-linear analytical function or may be performed by an artificial neural network. In most individuals, the blood glucose concentration can be linearly related to the ensemble of electrophysiological measurements. In other words, $[glucose]_{blood}$ is linear function of $\tilde{m}$, as shown in equation (4):

$$[glucose]_{blood}=c\tilde{m}^T_{preferred}=c_1\tilde{a}_{60}+c_2\tilde{a}_{180}+c_3\tilde{b}_{120}+c_4\tilde{b}_{240} \tag{4}$$

where T represents a vector transpose.

Equation (4) is used to rapidly and reliably translate the electrophysiological measurements made by the apparatus in steps 176 and 180 into the concurrent blood glucose concentration. This is achieved by multiplying a vector of correlation coefficients $c=\{c_1, c_2, c_3, c_4\}$ by the vector transpose of the measurement vector, in process step 190. Once the blood glucose concentration has been determined in the above-described manner, this blood glucose concentration is presented to the user by a user output device 22 (FIG. 1), such as alphanumeric display 36 (FIG. 2).

It is noted that the vector of correlation coefficients, $c=\{c_1, c_2, c_3, c_4\}$, is predetermined and stored in non-volatile memory within the microcontroller 20. This vector represents a mapping from the electrophysiological function of a hypoxic nerve, as characterized by the normalized measurement vector, $\tilde{m}$, to the blood glucose concentration, $[glucose]_{blood}$. More particularly, the coefficient vector, c, in equation (4) is obtained by a statistical analysis of a database of many pairs of simultaneously measured blood glucose concentration ($[glucose]_{blood}$) and nerve function ($\tilde{a}_{60}, \tilde{a}_{180}, \tilde{b}_{120}, \tilde{b}_{240}$) in a population of normal and diabetic individuals. The blood glucose concentration is determined using the generally accepted gold standard technique. At the present time, the most accurate measurements are performed in professional clinical laboratories by trained personnel using venous blood. The electrophysiological nerve function measurements are made by the apparatus of the present invention.

The optimal coefficient values (i.e. $\{c_1, c_2, c_3, c_4\}$ in equation 4) are determined by applying a multiple regression analysis or other multidimensional optimization procedure (e.g. Monte Carlo simulation or artificial neural network) to this database of simultaneously measured blood glucose and CAP parameters.

If the database is obtained from multiple individuals, further refinements of the coefficients can be made for specific individuals based on additional simultaneous blood glucose concentration and electrophysiological measurements in that individual alone. Alternatively, the database can be partitioned into groups according to characteristics of the diabetic population, such as age, sex, type of diabetes, and sets of corresponding coefficients provided for selection in accordance with characteristics of the user. This kind of coefficient "tuning" is only necessary in a small portion of individuals. As mentioned above, the coefficients are stored in non-volatile memory within the microcontroller 20 for real time calculation of the blood glucose concentration according to equation (4). The coefficients can also be updated at any time by replacing their values in memory.

Having described the preferred embodiments of the invention, it will be apparent to one of skill in the art that other embodiments incorporating their concepts may be used. Accordingly, the invention should be limited only by the spirit and scope of the appended claims.

I claim:

1. An apparatus for determining a concentration of an analyte in a user comprising:
   at least two stimulation electrodes adapted for applying an electrical stimulus having a predetermined strength for a predetermined duration to an endogenous tissue;
   a detection electrode adapted for detecting an electrical response of an endogenous tissue to said electrical stimulus to provide an electrical response signal; and
   a controller adapted for controlling the strength and duration of said electrical stimulus, and for correlating said response signal to an analyte concentration of said user, said controller producing an output which is a quantitative measure of said analyte concentration in response to said electrical response signal.

2. The apparatus recited in claim 1 wherein said analyte is a physiological analyte.

3. The apparatus recited in claim 2 wherein said physiological analyte is glucose.

4. The apparatus recited in claim 1 wherein said analyte is a non-physiological analyte.

5. The apparatus recited in claim 1, wherein said at least two stimulation electrodes are adapted for applying said electrical stimulus to a first endogenous tissue and said detection electrode is adapted for detecting said electrical response of a second endogenous tissue.

6. The apparatus recited in claim 1, wherein said at least two stimulation electrodes are adapted for applying said electrical stimulus to a first endogenous tissue and said detection electrode is adapted for detecting said electrical response from said first endogenous tissue.

7. The apparatus recited in claim 1 wherein said detection electrode comprises a plurality of detection electrodes.

8. The apparatus recited in claim 1 further comprising an occlusion mechanism for obstructing a flow of blood to said stimulated endogenous tissue or to said detected endogenous tissue.

9. The apparatus recited in claim 1 wherein said stimulated endogenous tissue is a nerve and said at least two stimulation electrodes are housed in a cuff adapted for securing to a finger of said user through which said nerve runs.

10. The apparatus recited in claim 9, wherein said cuff is adapted for being pressurized to provide an occlusion mechanism and to cause said at least two stimulation electrodes to contact said finger.

11. The apparatus recited in claim 9 wherein said at least one detection electrode is housed in said cuff.

12. The apparatus recited in claim 9 wherein said at least one detection electrode is housed in a wristband adapted for securing to a wrist of said user through which said nerve runs.

13. A glucose monitor comprising:
   a housing having a plurality of user actuable controls thereon;
   a controller disposed within said housing and responsive to actuation of said user actuable controls;
   a stimulator electrically connected to the controller and adapted to be in communication with a nerve of a user to stimulate said nerve with an electrical impulse in response to a stimulate command from said controller; and
   a detector electrically connected to said controller and adapted to be in communication with the nerve of said user to detect an electrical response of said nerve to said electrical impulse in response to a measure command from said controller and for providing said electrical response to said controller, wherein said controller produces an output which is a quantitative measure of said glucose concentration in response to said electrical response.

14. The monitor recited in claim 13, wherein said stimulate command and said measure command are generated by said controller in response to user actuation of a measurement control.

15. The monitor recited in claim 13, wherein said controller is adapted for generating said stimulate command and said measure command when said monitor is calibrated in order to determine a stimulus magnitude evoking a maximum detection sensitivity.

16. The monitor recited in claim 13 wherein said housing is adapted for connection to at least one of: a modem, a computer, and a memory device.

17. The monitor recited in claim 13 wherein said housing further comprises a display for visually displaying said glucose concentration.

18. The monitor recited in claim 13 wherein said housing further comprises a speaker for audibly indicating said glucose concentration.

* * * * *